(12) United States Patent
Lazar et al.

(10) Patent No.: US 10,240,137 B2
(45) Date of Patent: Mar. 26, 2019

(54) USE OF DIMERIZATION DOMAINS FOR TEMPERATURE REGULATION OF ENZYME ACTIVITY

(71) Applicant: Agrivida, Inc., Medford, MA (US)

(72) Inventors: Gabor Lazar, Belmont, MA (US); Jason Donald, Lexington, MA (US); R. Michael Raab, Arlington, MA (US)

(73) Assignee: AGRIVIDA, INC., Medford, MA (US)

( * ) Notice: Subject to any disclaimer, the term of this patent is extended or adjusted under 35 U.S.C. 154(b) by 0 days.

(21) Appl. No.: 14/774,954

(22) PCT Filed: Mar. 14, 2014

(86) PCT No.: PCT/US2014/028091
§ 371 (c)(1),
(2) Date: Sep. 11, 2015

(87) PCT Pub. No.: WO2014/152878
PCT Pub. Date: Sep. 25, 2014

(65) Prior Publication Data
US 2016/0024485 A1    Jan. 28, 2016

Related U.S. Application Data

(60) Provisional application No. 61/784,256, filed on Mar. 14, 2013.

(51) Int. Cl.
| | |
|---|---|
| *C12N 9/24* | (2006.01) |
| *C12N 15/56* | (2006.01) |
| *C07K 19/00* | (2006.01) |
| *C12N 9/42* | (2006.01) |

(52) U.S. Cl.
CPC ......... *C12N 9/2437* (2013.01); *C12N 9/2434* (2013.01); *C12N 9/2482* (2013.01); *C07K 2319/73* (2013.01); *C07K 2319/92* (2013.01); *C12Y 302/01004* (2013.01); *C12Y 302/01008* (2013.01)

(58) Field of Classification Search
None
See application file for complete search history.

(56) References Cited

U.S. PATENT DOCUMENTS

| | | |
|---|---|---|
| 2009/0197300 A1 | 8/2009 | Butler et al. |
| 2009/0280546 A1 | 11/2009 | Larossa |

FOREIGN PATENT DOCUMENTS

| | | |
|---|---|---|
| WO | 1996/016989 A1 | 6/1996 |
| WO | 2005/059084 A1 | 6/2005 |
| WO | 2009009142 A2 | 1/2009 |
| WO | 2012122308 A2 | 9/2012 |

OTHER PUBLICATIONS

Yuzama et al., Activating an enzyme by an engineered coiled coil switch, Chem. Eur. J., 2006, 12, 7345-7352.*
Ha et al., Modular Enzyme Design: Regulation by Mutually Exclusive Protein Folding, J. Mol. Biol., 2006, 357, 1058-62.*
Ostermeir, Designing switchable enzymes, Curr. Opin. Struct. Biol., 2009, 19, 442-48.*
Paes et al., GH11 xylanases, Biotechnol. Adv., 2012, 30, 564-92.*
Pack and Pluckthun, "Miniantibodies: Use of Amphipathic Helices to Produce Functional, Flexibly Linked Dimeric FV Fragments with High Avidity in *Escherichia coli*"; Biochemistry 1992, 31(6):1579-84; Abstract, p. 1581, Figure 1 and its legend; p. 1580, col. 2.
Motre et al., "Enhancing Helicase-Dependent Amplification by Fusing the Helicase with the DNA Polymerase"; Gene 2008, 420(1):17-22; p. 18, col. 1, Fig 1 and its legend.
Lohmueller, et al., "A Tunable Zinc Finger-Based Framework for Boolean Logic Computation in Mammalian Cells"; Nucleic Acids Res. 2012, 40(11): 5180-87; p. 5185, Figure 4 and its legend; pg. 5181, col. 1; p. 5181, col. 2.
Thompson, et al., "SYNZIP Protein Interaction Toolbox: in Vitro and in Vivo Specifications of Heterospecific Coiled-Coil Interaction Domains"; ACS Synth Biol. 2012, 1(4 ): 118-29; p. 121, col. 1; p. 122, col. 2; p. 123, Figure 3 and its legend, inset.
Azuma, et al., "Cobalt(II)-Responsive DNA Binding of a GCN4-bZIP Protein Containing Cysteine Residues Functionalized with Iminodiacetic Acid"; Angew. Chem. Int .Ed. 2009, 48(37):6853-6; p. 6853-56, col. 1 and Figure 1 and its legend; p. 6854, col. 2.
Wang, et al., "Improved Thermal Performance of Thermomyces Lanuginosus GH11 Xylanase by Engineering of an N-Terminal Disulfide Bridge"; Bioresource Technology 2012, 112:275-79; Abstract.
International Preliminary Report on Patentability issued in PCT/US14/028091 dated Sep. 9, 2014.
Hernandez Alvarez et al., 2008, "A new expression system for protein crystallization using trimeric coiled-coil adaptors," Protein Engineering, Design & Selection, 21(1): 11-18.
Yuzawa et al., 2006, "Activating an enzyme by an engineered coiled coil switch," Chem Eur J, 12 (28): 7345-7352.
Shen et al., 2012, "Engineering a thermoregulated intein-modified xylanase into maize for consolidated lignocellulosic biomass processing," Nature Biotechnology, 30(11): 1131-1136.
Donald et al., Aug. 1, 2012, "Engineering cell wall degrading enzymes with controllable activities," Protein Science, Willey, US, vol. 21, No. Suppl. 1, p. 171.
Supplementary European Search Report issued for EP patent application No. 14768375.9 dated Sep. 9, 2016.

(Continued)

*Primary Examiner* — Robert B Mondesi
*Assistant Examiner* — Todd M Epstein
(74) *Attorney, Agent, or Firm* — Volpe and Koenig, P.C.

(57) ABSTRACT

Methods for regulating protein activity by fusing dimerization domains to target protein are provided. Chimeric proteins that include dimerization domains fused to target proteins for altering the activity of the target proteins are described. Engineered nucleic acids encoding chimeric proteins and hosts engineered to express engineered nucleic acids are also provided.

12 Claims, 7 Drawing Sheets
Specification includes a Sequence Listing.

(56) References Cited

OTHER PUBLICATIONS

Amara et al. (1997) A versatile synthetic dimerizer for the regulation of protein-protein interactions. Proc. Natl. Acad. Sci. USA 94:10618-10623.

Armstrong et al. (2009) Rational design of peptide-based building blocks for nanoscience and synthetic biology. Faraday Discuss. 143: 305-317.

Armstrong et al. (2011) SCORER 2.0: An algorithm for distinguishing parallel dimeric and trimeric coiled-coil sequences. Bioinformatics 27(14):1908-1914.

Banwell et al. (2009) Rational design and application of responsive alpha-helical peptide hydrogels. Nat Mater 8: 596-600.

Bromley et al. (2010) Assembly Pathway of a Designed alpha-Helical Protein Fiber. Biophysical Journal 98(8), 1668-1676.

Bunagan et al. (2006) Truncation of a cross-linked GCN4-p1 coiled coil leads to ultrafast folding. Biochem 45(36):10981-6.

Burkhard et al. (2001) Coiled coils: a highly versatile protein folding motif. Trends Cell Bio 11(2):82-88.

Cutler et al. (2009) Effect of Interdomain Linker Length on an Antagonistic Folding-Unfolding Equilibrium between Two Protein Domains. J Mol Biol. 386(3): 854-868.

Fletcher et al. (2012) A Basis Set of de Novo Coiled-Coil Peptide Oligomers for Rational Protein Design and Synthetic Biology. ACS Synthetic Biology 6: 240-250.

Gagné et al. (2012) Conservation of flexible residue clusters among structural and functional enzyme homologues. J Biol Chem 287(53):44289-300.

Gray et al. (2011) Global and grain-specific accumulation of glycoside hydrolase family 10 xylanases in transgenic maize (*Zea mays*). Plant Biotechnol J. 9(9):1100-8.

Gruber et al. (1998) Thermophilic xylanase from Thermomyces lanuginosus: high-resolution X-ray structure and modeling studies. Biochem 37(39):13475-85.

Hadley et al. (2008) Preferred side-chain constellations at antiparallel coiled-coil interfaces. Proc. Natl. Acad. Sci. U. S. A. 105, 530-535.

Harbury et al. (1993) A switch between two-, three-, and four-stranded coiled coils in GCN4 leucine zipper mutants. Science 262(5138):1401-7.

Ellenberger et al. (1992) The GCN4 basic region leucine zipper binds DNA as a dimer of uninterrupted alpha helices: crystal structure of the protein-DNA complex. Cell 71:1223-1237.

Jones et al. (1996) Principles of protein-protein interactions. PNAS 93(1):13-20.

Landschulz et al. (1988) The leucine zipper: a hypothetical structure common to a new class of DNA-binding proteins. Science 240(4860): 1759-1764.

LoLeggio et al.(2002) The 1.62 Å structure of Thermoascus aurantiacus endoglucanase: completing the structural picture of subfamilies in glycoside hydrolase family 5. FEBS Lett 523(1-3):103-108.

Mason et al. (2004) Coiled coil domains: stability, specificity, and biological implications. Chembiochem 5 (2): 170-176.

Moutevelis et al. (2009) A periodic table of coiled-coil protein structures. Journal of Molecular Biology 385(3): 726-732.

Nagai et al.(2001) Circularly permuted green fluorescent proteins engineered to sense Ca2+. PNAS 98(6):3197-202.

O'Shea et al. (1989) Evidence that the leucine zipper is a coiled coil. Science 243: 538-542.

O'Shea et al. (1991) X-ray structure of the GCN4 leucine zipper, a two-stranded, parallel coiled coil. Science 254(5031):539-44.

O'Shea et al. (1993) Peptide 'velcro': design of a heterodimeric coiled coil. Current Biology 3(10):658-67.

Phillips et al. (2005) Scalable molecular dynamics with NAMD. J Comp Chem 26(16):1781-802.

Ramsden et al. (2011) An intein with genetically selectable markers provides a new approach to internally label proteins with GFP. BMC Biotechnology (11):71-82.

Russell et al. (2002) Use of certain alcohol ethoxylates to maintain protease stability in the presence of anionic surfactants. J Surfactants and Detergents 5(1):5-10.

Schlacher et al. (1996) Cloning and characterization of the gene for the thermostable xylanase XynA from Thermomyces lanuginosus. J Biotech 49:211-8.

Stauffer et al.(1973) Inactivation of subtilisin Carlsberg in surfactant and salt solutions. Biochem et Biophys Acta—Prot Str 295(2):457-66.

Shen et al. (2012) Engineering a thermoregulated intein-modified xylanase into maize for consolidated lignocellulosic biomass processing. Nature Biotech. 30(11):1131-6.

Spek et al. (1998) Surface salt bridges stabilize the GCN4 leucine zipper. Prot Sci 7(11):2431-37.

Spencer et al. (1993) Controlling signal transduction with synthetic ligands. Science. 262(5136):1019-24.

Spencer. (1996) Creating conditional mutations in mammals. Trends Genet. 12: 181-187.

Straussman et al. (2007) Kinking the coiled coil Å—negatively charged residues at the coiled-coil interface. J Mol Biol 366, 1232-1242.

Testa et al. (2009) CC+: a relational database of coiled-coil structures Nucleic Acid Research, vol. 37, Database issue, D315-D322.

Thatcher et al. (2012) A highly conserved effector in Fusarium oxysporum is required for full virulence on *Arabidopsis*. Mol Plant Microbe Interact. 25:180-190.

Villali et al. (2010) Choreographing an enzyme's dance. Curr. Op. Chem. Biol. 14(5):636-43.

Vincent et al. (2013) LOGICOIL—Multi-state prediction of coiled-coil oligomeric state. Bioinformatics 29(1):69-76.

Woolfson DN (2005) The design of coiled-coil structures and assemblies. Adv Prot Chem 70, 79-112.

Yu YB (2002) Coiled-coils: stability, specificity, and drug delivery potential. Adv Drug Deliv Rev 54 (8): 1113-1129.

Zhou et al. (2012) Optical control of protein activity by fluorescent protein domains. Science. 338(6108):810-4.

Zitzewitz (2000) Preformed secondary structure drives the association reaction of GCN4-p1, a model coiled-coil system. J Mol Bio. 296(4):1105-16.

\* cited by examiner

USE OF DIMERIZATION DOMAINS FOR TEMPERATURE REGULATION OF ENZYME ACTIVITY

CROSS REFERENCE TO RELATED APPLICATIONS

This application is a 35 U.S.C. § 371 national stage application of PCT/US2014/28091, which was filed Mar. 14, 2014 and claims the benefit of U.S. Provisional Application No. 61/784,256, filed Mar. 14, 2013, both of which are incorporated by reference as if fully set forth.

The sequence listing electronically filed with this application titled "Sequence Listing," which was created on Mar. 14, 2014 and had a size of 55,678 bytes is incorporated by reference herein as if fully set forth.

FIELD

The disclosure relates to methods of regulating enzyme activity or protein functionality using chimeric proteins that include dimerization domains fused to target proteins. Chimeric proteins and isolated nucleic acids encoding the chimeric proteins are also disclosed.

BACKGROUND

Enzymes are widely used in industry to convert one chemical substance into another, e.g. degrading proteins into amino acids (proteases) or producing sugar from plant cell walls (hydrolytic enzymes). While a constitutively active enzyme is generally useful in industrial settings, in specific applications it can be beneficial to tightly control enzyme activity. For example, if a protease can be inactivated while in storage, it will not autodegrade (Stauffer and Treptow 1973, Russell and Britton 2002). For hydrolytic enzymes expressed in plants, enzyme activity during growth can harm the plant (Gray et al. 2011, Shen et al. 2012). If the enzyme is inactivated until the plant is harvested, then the plant can grow normally. Upon activation the enzyme can degrade the plant cell wall. In many cases, temperature can act as a convenient exogenously controllable parameter of a system.

Controlled dimerization has previously been used to bring together two different proteins, change the fluorescence character of a protein, or block the accessibility of a substrate binding pocket (Spencer et al. 1993; Nagai et al. 2001; Zhou et al. 2012). Chemical inducers of dimerization have been used effectively to control transcription of target genes, triggering specific signal transduction, and recruit proteins (Spencer et al. 1993; Spencer 1996; Amara et al., 1997).

SUMMARY

In an aspect, the invention relates to a chimeric protein comprising a target protein, a first dimerization domain and a second dimerization domain. The first dimerization domain is fused to the target protein. The second dimerization domain is fused to the target protein, the first dimerization domain interacts with the second dimerization domain to alter the activity of the target protein. The first dimerization domain is selected from the group consisting of: a coiled-coil dimerization domain GCN4, ATF6, CREB1, C/EBPα, Fos, Jun, influenza hemagglutinin, and HIVgp41. The second dimerization domain is selected from the group consisting of: a coiled-coil dimerization domain GCN4, ATF6, CREB1, C/EBPα, Fos, Jun, influenza hemagglutinin, and HIVgp41.

In an aspect, the invention relates to an engineered nucleic acid encoding a chimeric protein. The chimeric protein includes a target protein that includes a first dimerization domain and a second dimerization domain. The first dimerization domain is fused to the target protein. The second dimerization domain is fused to the target protein. The first dimerization domain interacts with the second dimerization domain to alter the activity of the target protein. The first dimerization domain is selected from the group consisting of: a coiled-coil dimerization domain GCN4, ATF6, CREB1, C/EBPα, Fos, Jun, influenza hemagglutinin, and HIVgp41. The second dimerization domain is selected from the group consisting of: a coiled-coil dimerization domain GCN4, ATF6, CREB1, C/EBPα, Fos, Jun, influenza hemagglutinin, and HIVgp41.

In an aspect, the invention relates to a vector that includes any one of the engineered nucleic acids described herein.

In an aspect, the invention relates to a host that includes any one of the engineered nucleic acids described herein.

In an aspect, the invention relates to a method of regulating the activity of a target protein. The method includes engineering a chimeric protein that includes a target protein, a first dimerization domain, a second dimerization domain. The first dimerization domain is fused to the target protein. The second dimerization domain is fused to the target protein. The first dimerization domain interacts with the second dimerization domain to alter the activity of the target protein. The first dimerization domain is selected from the group consisting of: a coiled-coil dimerization domain GCN4, ATF6, CREB1, C/EBPα, Fos, Jun, influenza hemagglutinin, and HIVgp41. The second dimerization domain is selected from the group consisting of: a coiled-coil dimerization domain GCN4, ATF6, CREB1, C/EBPα, Fos, Jun, influenza hemagglutinin, and HIVgp41.

In an aspect, the invention relates to a method of regulating the activity of a target protein within a chimeric protein. The chimeric protein includes the target protein, a first dimerization domain fused to the target protein, and a second dimerization domain fused to the target protein. The first dimerization domain interacts with the second dimerization domain to alter the activity of the target protein. The method includes exposing the chimeric protein to a triggering condition to disrupt interaction of the first dimerization domain and the second dimerization domain. The first dimerization domain is selected from the group consisting of: a coiled-coil dimerization domain GCN4, ATF6, CREB1, C/EBPα, Fos, Jun, influenza hemagglutinin, and HIVgp41. The second dimerization domain is selected from the group consisting of: a coiled-coil dimerization domain GCN4, ATF6, CREB1, C/EBPα, Fos, Jun, influenza hemagglutinin, and HIVgp41.

BRIEF DESCRIPTION OF THE DRAWINGS

The following detailed description of embodiments of the present invention will be better understood when read in conjunction with the appended drawings. For the purpose of illustration, there are shown in the drawings embodiments which are presently preferred. It is understood, however, that the invention is not limited to the precise arrangements and instrumentalities shown. In the drawings.

DETAILED DESCRIPTION OF EMBODIMENTS

Figure 1:
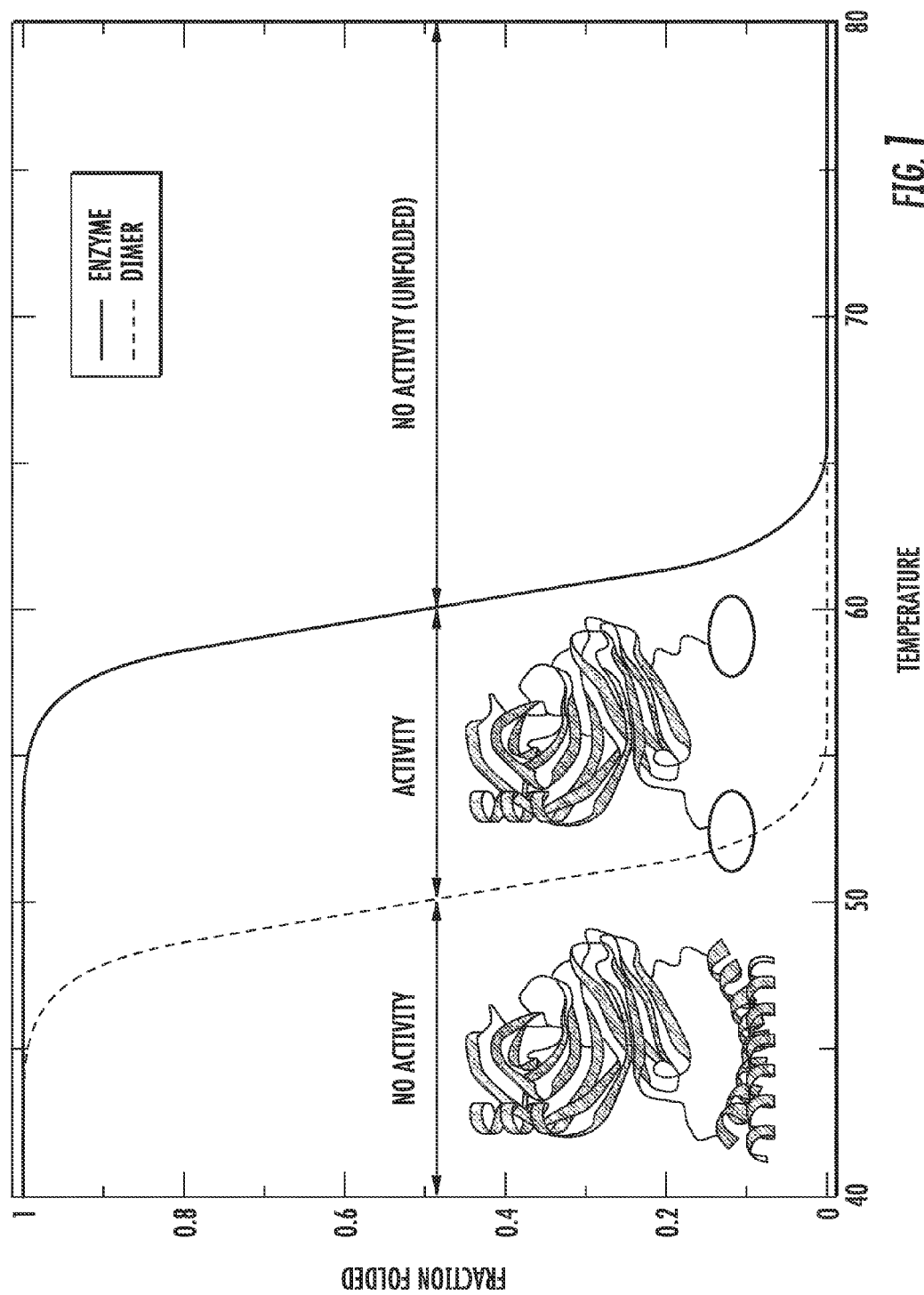
FIG. 1 illustrates controllable dimmer-induced protein regulation.

Certain terminology is used in the following description for convenience only and is not limiting.

"Engineered nucleic acid," "engineered polynucleotide," "engineered oligonucleotide," "engineered DNA," or "engineered RNA" as used herein refers to a synthetic nucleic acid, polynucleotide, oligonucleotide, DNA, or RNA.

The words "right," "left," "top," and "bottom" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

A technology where enzyme activity is controlled by temperature may increase the value of target enzymes and allow their use in additional industrial settings. To be active, an enzyme may change its three-dimensional structure to bind a ligand, reach a transition state structure, and release the product (Villali and Kern 2010). If an enzyme is limited in its ability to change its three-dimensional structure, it will be less able to accommodate the steps necessary for catalysis (Gagne et al. 2012). One way of limiting the ability of an enzyme to change its three-dimensional structure is to constrain a region that is likely to change position during the enzymatic reaction. Fusion of controllable protein dimerization domains to the enzyme may constrain the enzyme and inhibit enzyme function when the dimer is formed but allow the enzyme to be active when the dimerization domains are disrupted.

In an embodiment, a chimeric protein comprising a target protein, a first dimerization domain and a second dimerization domain is provided. The first dimerization domain may be fused to the target protein. The second dimerization domain may be fused to the target protein. The first dimerization domain may interact with the second dimerization domain to alter the activity of the target protein. The first dimerization domain may be selected from the group consisting of: a coiled-coil dimerization domain GCN4, ATF6, CREB1, C/EBPα, Fos, Jun, influenza hemagglutinin, and HIVgp41. The second dimerization domain may be selected from the group consisting of: a coiled-coil dimerization domain GCN4, ATF6, CREB1, C/EBPα, Fos, Jun, influenza hemagglutinin, and HIVgp41.

As used herein, the term "dimerization domains" refers to proteins capable of forming a dimer, or undergo dimerization. Most dimers are not connected by covalent bonds. A dimer may be a homodimer formed by two identical dimerization domains. A dimer may be a heterodimer formed by two different dimerization domains. Dimerization domains are ubiquitous in proteins, and their dimerization can be controlled by many different factors including temperature, ligand binding, and light. See Jones and Thornton 1996, which is incorporated herein by reference as if fully set forth.

In an embodiment, the first dimerization domain, or the second dimerization domain may be any known dimerization domain. One of the best known protein dimerization motifs is the coiled coil, a common domain in various transcription factors viral proteins, and elsewhere that consists of hydrophobic residues found in a 7 amino acid (heptad) periodicity. See Landschulz et al., 1988, which is incorporated herein by reference as if fully set forth. The periodic hydrophobic residues form the core of the hydrophobic dimer interface. Extensive work on the coiled coil motif of the GCN4 transcription factor involving careful perturbation of the sequence makes the coiled coil particularly amenable to design novel dimerization properties. See O'Shea et al, 1989, 1991, 1993; Harbury et al. 1993, all of which are incorporated by reference as if fully set forth. The first dimerization domain, or the second dimerization domain may be the coiled coil dimerization domain. The coiled coil dimerization domain may be the GCN4 transcription factor.

In an embodiment, dimerization domains may be coiled coils from other basic leucine zippers. The other basic leucine zippers may be TF6, CREB1, C/EBPα, Fos, or Jun, viral fusion proteins influenza hemagglutinin or HIV gp41, or other coiled coil domains APC or ProP. Dimerization domains may be thermo-sensitive dimeric coiled coils or more complex multimeric coil structures in recombinant proteins as a simple, efficient and versatile means to regulate enzyme activity both in vivo and in vitro.

Dimerization domains are not limited to coil-coils. Any dimerization domain may be used for development of a switch. A compilation of known dimerization domains is provided on the following websites: http://coiledcoils.chm-.bris.ac.uk/ccplus/search/ and http://www.chm.bris.ac.uk/org/ woolfson/oli.html; and has been described in Testa O D, Moutevelis E, and Woolfson D N, 2009, "CC+: a relational database of coiled-coil structures," Nucleic Acid Research, Vol. 37, Database issue, D315-D322; Moutevelis E and Woolfson, D N, 2009, "A periodic table of coiled-coil protein structures," Journal of Molecular Biology 385(3): 726-732, all of which are incorporated by reference herein as if fully set forth. Additionally, coiled coil structures were described in Vincent, T L, Green P J and Woolfson D N, 2013, "LOGICOIL—Multi-state prediction of coiled-coil oligomeric state," Bioinformatics 29(1):69-76; Armstrong C R, Vincent T L, Green P J and Woolfson D N, 2011, "SCORER 2.0: An algorithm for distinguishing parallel dimeric and trimeric coiled-coil sequences," Bioinformatics 27(14):1908-1914; Woolfson D N, 2005, "The design of coiled-coil structures and assemblies," Adv. Prot. Chem. 70, 79-112; Mason J M, and Arndt K M, 2004, "Coiled coil domains: stability, specificity, and biological implications," Chembiochem 5 (2): 170-176; Yu Y B, 2002, "Coiled-coils: stability, specificity, and drug delivery potential," Adv. Drug Deliv. Rev. 54 (8): 1113-1129; Brown J H, 2006, "Breaking symmetry in protein dimers: designs and functions," Protein Sci. 15(1): 1-13; Straussman R, Ben-Ya'acov A, Woolfson D N, and Ravid S, 2007 "Kinking the coiled coil Â-negatively charged residues at the coiled-coil interface," J. Mol. Biol. 366, 1232-1242; Armstrong C T, Boyle A L, Bromley E H C, Mahmoud Z N, Smith L, Thomson A R, and Woolfson D N, 2009, "Rational design of peptide-based building blocks for nanoscience and synthetic biology," Faraday Discuss. 143, 305-317; Banwell E F, Abelardo E S, Adams D J, Birchall M A, Corrigan A, Donald A M, Kirkland M, Serpell L C, Butler M F, and Woolfson D N, 2009 "Rational design and application of responsive alpha-helical peptide hydrogels," Nat. Mater. 8: 596-600; Fletcher D M, Boyle A L, Bruning M, Bartlett G J, Vincent T L, Zaccai N R, Armstrong C T, Bromley E H C, Booth P J, Brady R L, Thomson A R, and Woolfson D N, 2012 "A Basis Set of de Novo Coiled-Coil Peptide Oligomers for Rational Protein Design and Synthetic Biology," ACS Synthetic Biology 6: 240-250; Bromley E H C, Channon K J, King P J S, Mahmoud Z N, Banwell E F, Butler M F, Crump M P, Dafforn T E, Hicks D M R, Hirst J D, Rodger A and Woolfson D N, 2010 "Assembly Pathway of a Designed alpha-Helical Protein Fiber," Biophysical Journal 98(8), 1668-1676; Hadley E B, Testa O D, Woolfson D N, and Gellman S H, 2008, "Preferred side-chain constellations at antiparallel coiled-coil interfaces," Proc. Natl. Acad. Sci. U.S.A 105, 530-535, all of which are incorporated by reference herein as if fully set forth Other dimerization domains may be discovered and new dimerization domains may be created through sequence analysis, recombinant DNA methods, and mutation of known sequences.

In an embodiment, dimerization domains may be dimerization domains other than coiled coils. Dimerization domains may be, but are not limited to, membrane dimerization domains, dimerization domains from transcription factors other than leucine zippers, G protein $\beta_\gamma$ complexes from heterotrimeric G protein complexes, TIM, ADH5, 14-3-3 proteins or their binding partners Bad or Bax, or other protein dimers. Membrane dimerization domains may be glycophorin A, receptor tyrosine kinases, or GPCRs. Dimerization domains from transcription factors other than leucine zippers may be nuclear receptors, an estrogen receptor, an androgen receptor, a glucocorticoid receptor, basic helix-loop-helix MyoD or c-Myc, helix-turn-helix LuxR, TetR, or cI.

In an embodiment, the first dimerization domain, or the second dimerization domain may be included in a sequence with at least at least 70, 72, 75,80, 85, 90, 91, 92, 93, 94, 95, 96, 97, 98, 99, or 100% identity to SEQ ID NO: 2 [GCN4].

In an embodiment, the target protein may be any protein with activity which needs to be altered. The activity to be altered may be an undesirable activity. A target protein may be an enzyme. As used herein, the term "target enzyme" means a "target protein" that is an enzyme. The target proteins may be but are not limited to enzymes, transcription factors, membrane channels, membrane transporters, antibodies, hormonal proteins, or other proteins. Enzymes may be hydrolases, amylases, mannanases, xylanases, cellulases, proteases, lipases, kinases, catalases, or restriction enzymes. Hydrolases may be but are not limited to proteases, glycosyl hydrolyses, or amylases. The protease may be an enzyme classified under EC 3.4 as peptide hydrolases. Proteases may include those classified under EC 3.4.99, EC 3.4.21.62, serine proteases, alkaline proteases, keratinases, and others. Other proteases that may include but are not limited to metallo proteases, cysteine proteases, aspartate proteases, and ATP-dependent proteases, proteases of Subtilisin family, Savinase, P29600 and Keratinase Q53521. Amylases may be but are not limited to α-amylases, β-amylases, isoamylases, or glucoamylases. Isoamylases may include but not limited to ISA3. Glycosyl hydrolases may be but are not limited to endo-beta-glucosidases, or exo-glucanases. A target enzyme may be any other enzyme.

In an embodiment, the target protein may include a sequence with at least 70, 72, 75, 80, 85, 90, 91, 92, 93, 94, 95, 96, 97, 98, 99, or 100% identity to SEQ ID NO: 1 [O43T] or SEQ ID NO: 14 [BD25243].

The target protein may be an intein. The intein may be but is not limited to Tth, mTth, Psp-pol, Mtu RecA, Sce VMA, Pho-RecA, or Tko_RecA. The target protein may be an intein-modified protein.

In an embodiment, the first dimerization domain, or the second dimerization domain may be fused to the N-terminus or the C-terminus of the target protein. The first dimerization domain may be fused to the target protein by a first linker. The second linker may be contiguous with and between the first dimerization domain and the target protein. The second dimerization domain may be fused to the target protein by a second linker. The second linker may be contiguous with and between the second dimerization domain and the target protein.

The first linker or the second linker may be any linker. The first linker or the second linker may be an amino acid linker. The first linker or the second linker may be a linker an appropriate length. The linker of the appropriate length may be a linker suitable for dimer formation that causes the disruption of the structure of the target protein. A non-limiting test to select a linker can be found in one or more of Examples 4-12 herein. The test includes determining whether a linker is of a suitable length for dimer formation. The appropriate length may range from zero to dozens of amino acids depending on the structure of the dimerization domain and the structure of the target protein. The appropriate length may be a minimal length that produces the desired target protein characteristics. The first linker or the second linker may be a linker that acts as a molecular spring that causes disruption within the target protein when the dimer is formed but may allow the target protein to return to a normal conformation when the dimer is disrupted. The first linker or the second linker may be a linker designed to incorporate secondary modification sites. The secondary modification sites may be but are not limited to protease recognition sites. The protease recognition sites may modulate functionality in vivo. The first linker or the second linker may be a linker designed using protein modeling and further improved through mutagenesis. The linker designed using modeling may connect the one or more dimerization domains to the target protein. Modeling may include loop modeling, molecular dynamics simulations, homology modeling, fixed backbone protein design and flexible backbone protein design. The first linker or the second linker may be a linker expressed and tested experimentally.

The N-terminus of the second dimerization domain may be linked to and contiguous with the C-terminus of the target protein. The C-terminus of the first dimerization may be linked to and contiguous with the N-terminus of the target protein, and the N-terminus of the second dimerization domain may be linked to and contiguous with the C-terminus of the target protein.

The first dimerization domain may be fused to the target protein internally. The second dimerization domain may be fused to the target protein internally. Both the first dimerization domain and the second dimerization domain may be fused to the target protein internally. The first dimerization domain may be fused to the target protein terminally, and the second dimerization domain may be fused to the target protein internally. The first dimerization domain may be fused to the target protein internally and the second dimerization domain may be fused to the target protein terminally.

In an embodiment, the first dimerization domain or the second dimerization domain may be covalently linked to the target protein.

In an embodiment, there may be more than two dimerization domains.

In an embodiment, a chimeric protein may include a sequence with at least 70, 72, 75, 80, 85, 90, 91, 92, 93, 94, 95, 96, 97, 98, 99, or 100% identity to a reference sequence selected from the group consisting of: SEQ ID NO: 3 [CC1], SEQ ID NO: 4 [CC2], SEQ ID NO: 5 [CC17], SEQ ID NO: 6 [CC13], SEQ ID NO: 7[CC14-1], SEQ ID NO: 8[CC14-2], SEQ ID NO: 9 [CC15], SEQ ID NO: 10 [CC22], SEQ ID NO: 11[CC23], SEQ ID NO: 12 [CC24], SEQ ID NO: 13 [CC30], and SEQ ID NO: 15 [BD25CC2].

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity may be measured by the Smith Waterman algorithm (Smith T F, Waterman M S 1981 "Identification of Common Molecular Subsequences," J Mol Biol 147: 195-197, which is incorporated herein by reference as if fully set forth). Percent identity refers to the percent measured along the length of a reference sequence.

In an embodiment, the activity of the target protein may be repressed. The interaction between the first dimerization domain and the second dimerization domain may be capable of being disrupted upon exposure of the chimeric protein to a triggering condition. Disruption of the interaction may reactivate the activity of the target protein.

The triggering condition may be but is not limited to a triggering temperature, a triggering pH, a triggering ligand binding, a triggering light, a triggering ion, a triggering concentration of an ion, a triggering sound, a triggering compound, or a triggering concentration of a compound.

In an embodiment, the triggering condition may be a triggering temperature. The triggering temperature may be a temperature range where the first dimerization domain or the second dimerization domain is bound within the chimeric protein. The triggering range may be a temperature range where the first dimerization domain or the second dimerization domain is unbound or less stably bound within the chimeric protein. The triggering temperature may include a range of temperatures if the target protein is active over a range of temperatures that overlaps with both the bound and unbound temperatures of the dimerization domains. The triggering temperature may be a switch to control both the dimerization of the coiled coil domains and the activity of the enzyme. The triggering temperature may include a temperature of 30° C. to 70° C., or more. The triggering temperature of 30° C. to 70° C. may allow dimerization domains to be unbound or less stably bound within the chimeric protein to. The triggering temperature of 30° C. to 70° C. may allow reactivation of the activity of the target protein. The triggering temperature may be a temperature of 30° C., 31° C., 32° C., 33° C., 34° C. 35° C., 36° C., 37° C., 38° C., 39° C., 40° C., 41° C., 42° C., 43° C., 44° C. 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C. 70° C., 75° C., 80° C., 85° C., 90° C., 95° C., 100° C., 30° C. to 45° C., 30° C. to 55° C., 30° C. to 65° C., 30° C. to 75° C., 30° C. to 75° C., 30° C. to 95° C., 30° C. to less than 100° C., 30° C. to 65° C., 30° C. to 75° C., 30° C. to 95° C., 30° C. to less than 100° C., 65° C. to 75° C., 65° C. to 95° C., 65° C. to less than 100° C., 75° C. to 95° C., 75° C. to less than 100° C., or 95° C. to less than 100° C. The triggering temperature may be less than any one of the foregoing values.

In an embodiment, the triggering condition may be a triggering pH. The triggering pH may be greater than or equal to pH 4. The triggering pH may be a pH greater than or equal to pH 4, 5, 6, 7, 8, 9, or 10, or greater than or equal to any value in a range between any two of the foregoing pH values. The triggering pH may be a pH lower than pH 10, 9, 8, 7, 6, 5, or 4, or lower than any value in a range between any two of the foregoing pH values.

In an embodiment, the triggering condition may be a triggering concentration of a substance. The substance may be a triggering ion or a triggering compound. The triggering concentration may be 1M, 0.9M, 0.8M, 0.7M, 0.6M, 0.5M, 0.4M, 0.3M, 0.2M, 0.1M, or 0.05 M, or concentration in a range between any two of the foregoing molar values. The triggering concentration may be less than any one of the foregoing values.

In an embodiment, the triggering condition may be the presence of a triggering ion. The triggering ion may be a triggering cation. The triggering cation may be a divalent cation. The divalent cation may be but is not limited to $Zn^{2+}$, $Ca^{2+}$, $Fe^{2+}$, or $Mg^{2+}$. There may be other triggering divalent cations.

In an embodiment, the triggering condition may be the presence of a triggering compound. The triggering compounds may be but are not limited to detergent alcohols, salts, or organic acids. The detergent alcohol may be but is not limited to monoethanolamine (MEA), triethanolamine (TEA) or Neodol 25-7. The triggering compounds may be other detergent alcohols. The organic acid may be but is not limited to citric acid, lactic acid, phosphoric acid, succinic acid, palmitic acid, or linear alkylbenzen sulfonic acid (LAS acid). The triggering compounds may be other acids. Other acids may be distilled fatty acids, 1-hydroxyethylidene-1,1-diphophoric acid, HCl, or sulfuric acid. Distilled fatty acids may include Prifac. The 1-hydroxyethylidene-1,1-diphophoric acid may be HEDP or Dequest 2010. The triggering salt may be but is not limited to sodium lauryl ether sulphate, or sodium sulphite. There may be other triggering compounds.

In an embodiment, the activity of the target protein may be enhanced. The interaction between the first dimerization domain and the second dimerization domain may be capable of being disrupted upon exposure of the chimeric protein to a triggering condition. The disruption of the interaction may disrupt the enhanced activity of the target protein. The triggering condition may be any triggering condition described herein. The enhanced activity may be improved thermostability of the target protein.

In an embodiment, an engineered nucleic acid encoding a chimeric protein is provided. The chimeric protein may include a target protein, a first dimerization domain and a second dimerization domain. The first dimerization domain may be fused to the target protein. The second dimerization domain may be fused to the target protein. The first dimerization domain may interact with the second dimerization domain to alter the activity of the target protein. The first dimerization domain may be selected from the group consisting of: a coiled-coil dimerization domain GCN4, ATF6, CREB1, C/EBPα, Fos, Jun, influenza hemagglutinin, and HIVgp41. The second dimerization domain may be selected from the group consisting of: a coiled-coil dimerization domain GCN4, ATF6, CREB1, C/EBPα, Fos, Jun, influenza hemagglutinin, and HIVgp41.

The engineered nucleic acid may include a sequence encoding the target protein. The engineered nucleic acid may include a sequence having at least 70, 72, 75, 80, 85, 90, 91, 92, 93, 94, 95, 96, 97, 98, 99, or 100% identity to SEQ ID NO: 16 [O43 T] or SEQ ID NO: 29 [BD25243].

The engineered nucleic acid may include a sequence that encodes at least the first dimerization domain, or the second dimerization domain. The engineered nucleic acid may include a sequence having at least 70, 72, 75, 80, 85, 90, 91, 92, 93, 94, 95, 96, 97, 98, 99, or 100% identity to SEQ ID NO: 17 [GCN4].

The engineered nucleic acid may include a sequence with at least 70, 72, 75, 80, 85, 90, 91, 92, 93, 94, 95, 96, 97, 98, 99, or 100% identity to a reference sequence selected from the group consisting of: SEQ ID NO: 18[CC1], SEQ ID NO: 19 [CC2], SEQ ID NO: 20 [CC17], SEQ ID NO: 21 [CC13], SEQ ID NO: 22[CC14-1], SEQ ID NO: 23[CC14-2], SEQ ID NO: 24 [CC15], SEQ ID NO: 25 [CC22], SEQ ID NO: 26 [CC23], SEQ ID NO: 27 [CC24], SEQ ID NO: 28 [CC30], and SEQ ID NO: 30 [BD25CC2].

In an embodiment, engineered nucleic acids are provided having a sequence as set forth in any one of the nucleic acids listed herein or the complement thereof. In an embodiment, engineered nucleic acids having a sequence that hybridizes to a nucleic acid having the sequence of any nucleic acid listed herein or the complement thereof are provided. In an embodiment, the hybridization conditions are low stringency conditions. In an embodiment, the hybridization conditions are moderate stringency conditions. In an embodiment, the hybridization conditions are high stringency conditions. Examples of hybridization protocols and methods for optimization of hybridization protocols are described in the following books: Molecular Cloning, T. Maniatis, E. F. Fritsch, and J. Sambrook, Cold Spring Harbor Laboratory, 1982; and, Current Protocols in Molecular Biology, F. M. Ausubel, R. Brent, R. E. Kingston, D. D. Moore, J. G. Seidman, J. A. Smith, K. Struhl, Volume 1, John Wiley & Sons, 2000, which are incorporated by reference in their entirety as if fully set forth. Moderate conditions may be as follows: filters loaded with DNA samples are pretreated for 2-4 hours at 68° C. in a solution containing 6×citrate buffered saline (SSC; Amresco, Inc., Solon, Ohio), 0.5% sodium dodecyl sulfate (SDS; Amresco, Inc., Solon, Ohio), 5×Denhardt's solution (Amresco, Inc., Solon, Ohio), and denatured salmon sperm (Invitrogen Life Technologies, Inc. Carlsbad, Calif.). Hybridization is carried in the same solution with the following modifications: 0.01 M EDTA (Amresco, Inc., Solon, Ohio), 100 μg/ml salmon sperm DNA, and 5-20×10$^6$ cpm $^{32}$P-labeled or fluorescently labeled probes. Filters are incubated in hybridization mixture for 16-20 hours and then washed for 15 minutes in a solution containing 2×SSC and 0.1% SDS. The wash solution is replaced for a second wash with a solution containing 0.1×SSC and 0.5% SDS and incubated an additional 2 hours at 20° C. to 29° C. below Tm (melting temperature in ° C.). Tm=81.5+16.61 Log$_{10}$([Na$^+$]/(1.0+0.7[Na$^+$]))+0.41(% [G+C])−(500/n)−P−F. [Na+]=Molar concentration of sodium ions. %[G+C]=percent of G+C bases in DNA sequence. N=length of DNA sequence in bases. P=a temperature correction for % mismatched base pairs (~1° C. per 1% mismatch). F=correction for formamide concentration (=0.63° C. per 1% formamide). Filters are exposed for development in an imager or by autoradiography. Low stringency conditions refers to hybridization conditions at low temperatures, for example, between 37° C. and 60° C., and the second wash with higher [Na$^+$] (up to 0.825M) and at a temperature 40° C. to 48° C. below Tm. High stringency refers to hybridization conditions at high temperatures, for example, over 68° C., and the second wash with [Na+] =0.0165 to 0.0330M at a temperature 5° C. to 10° C. below Tm.

In an embodiment, engineered nucleic acids having a sequence that has at least 70, 72, 75, 80, 85, 90, 91, 92, 93, 94, 95, 96, 97, 98, 99 or 100% identity along its length to a contiguous portion of a nucleic acid having any one of the sequences set forth herein or the complements thereof are provided. The contiguous portion may be the entire length of a sequence set forth herein or the complement thereof.

In an embodiment, engineered nucleic acids, polynucleotides, or oligonucleotides are provided having a portion of the sequence as set forth in any one of the nucleic acids listed herein or the complement thereof. These engineered nucleic acids, polynucleotides, or oligonucleotides are not limited to but may have a length in the range from 10 to full length, 10 to 1300, 10 to 1200, 10 to 1100, 10 to 1000, 10 to 900, 10 to 800, 10 to 10 to 600, 10 to 500, 10 to 400, 10 to 300, 10 to 200, 10 to 100, 10 to 90, 10 to 80, 10 to 70, 10 to 60, 10 to 50, 10 to 40, 10 to 35, 10 to 30, 10 to 25, 10 to 20, 10 to 15, or 20 to 30 nucleotides or 10, 15, 20 or 25 nucleotides. An engineered nucleic acid, polynucleotide, or oligonucleotide having a length within one of the above ranges may have any specific length within the range recited, endpoints inclusive. The recited length of nucleotides may start at any single position within a reference sequence (i.e., any one of the nucleic acids herein) where enough nucleotides follow the single position to accommodate the recited length. In an embodiment, a hybridization probe or primer is 85 to 100%, 90 to 100%, 91 to 100%, 92 to 100%, 93 to 100%, 94 to 100%, 95 to 100%, 96 to 100%, 97 to 100%, 98 to 100%, 99 to 100%, or 100% complementary to a nucleic acid with the same length as the probe or primer and having a sequence chosen from a length of nucleotides corresponding to the probe or primer length within a portion of a sequence as set forth in any one of the nucleic acids listed herein. In an embodiment, a hybridization probe or primer hybridizes along its length to a corresponding length of a nucleic acid having the sequence as set forth in any one of the nucleic acids listed herein. In an embodiment, the hybridization conditions are low stringency. In an embodiment, the hybridization conditions are moderate stringency. In an embodiment, the hybridization conditions are high stringency.

In an embodiment, a vector is provided. The vector may include any one of the engineered nucleic acids described herein. A vector may be used to genetically engineer a host to express any one of the chimeric proteins described herein.

In an embodiment, a host that includes any one of the engineered nucleic acids described herein is provided.

In an embodiment, a host may include any one of the chimeric proteins described herein.

The host may be but is not limited to microorganism, a phage, a virus, a mammalian cell, a plant cell and an insect cell. The host may be a plant.

In an embodiment a method of regulating the activity of a target protein is provided. The method may include engineering a chimeric protein by fusing a first dimerization domain, and a second dimerization domain to a target protein. Within the chimeric protein, dimerization domains may interact and alter the activity of the target protein.

In an embodiment, a method of regulating the activity of a target protein is provided. The method may include engineering a chimeric protein that includes a target protein, a first dimerization domain, a second dimerization domain. The first dimerization domain may be fused to the target protein, the second dimerization domain may be fused to the target protein. The first dimerization domain may interact with the second dimerization domain to alter the activity of the target protein. The first dimerization domain may be selected from the group consisting of: a coiled-coil dimerization domain GCN4, ATF6, CREB1, C/EBPα, Fos, Jun, influenza hemagglutinin, and HIVgp41. The second dimerization domain may be selected from the group consisting of: a coiled-coil dimerization domain GCN4, ATF6, CREB1, C/EBPα, Fos, Jun, influenza hemagglutinin, and HIVgp41.

The step of engineering may include making an expression construct that includes a nucleic acid encoding the chimeric protein.

The step of making the expression construct may include analyzing an amino acid sequence of the target protein for functionally active regions based on proximity to structures selected from the group consisting of: disulfide bridges, catalytic domains, ligand binding domains, and sites accessible to solvents.

The step of making the expression construct may include selecting the insertion site for the first dimerization domain or the second dimerization domain within a target protein. The insertion sites may be selected based on one or more factors. The insertion sites may be selected based three-dimensional separation of dimerization domains in the structure of the target protein. The three-dimensional separation of dimerization domains in a target protein may be selected by using appropriate linkers to connect the target protein and the one or more dimerization domains such that the target protein can remain well-folded. The target protein dynamics may be largely restrained when the dimer is formed, but may have less restrained protein dynamics when the dimer is not formed. The insertion sites may be selected based avoidance of sites where insertions are likely to disrupt the target protein stability or function. The insertion sites may be selected at positions where the tension of dimer formation may disrupt target protein dynamics and function. The insertion sites may be selected at positions where the monomer state of the dimerization domains would not be disruptive to the structure of the target protein. The insertion sites may be selected based on stability of the target protein. The insertion sites may be selected based secondary structure of the site, solvent accessibility of the site, amino acid identity of the surrounding residues, proximity to disulfide bridges and proximity to catalytic, ligand binding, or other functionally active regions of the target protein should. The insertion sites may be selected by using protein modeling. Protein modeling may be used to select sites where insertions are unlikely to substantially change the stability or function of the target protein when the dimer is not formed.

The method may further include inserting a nucleic acid that encodes the first dimerization domain, or the second dimerization domain in the nucleic acid encoding the target protein in such a position that effects interaction of the domains and alters the activity of the target protein. The two dimerization domains may be inserted into distinct regions of the target protein that are in proximity to each other in the folded protein structure. Three-dimensional proximity may allow the dimerization domains to form a dimeric structure within the target protein. By transitioning from a constrained state to an unconstrained or less constrained state, dimerization can act as a switch to control target function of the target protein. FIG. 1 shows that when the dimerization domain associates, the enzyme cannot carry out catalysis efficiently, but when dimerization is disrupted, the enzyme may be free to catalyze its target substrate. For single domain proteins, the dimerization domain may be placed at both termini of the target protein. For multidomain proteins, dimerization domain may be placed at the termini, internally between domains or in a combination of terminal and internal locations. The dimerization domains may be coiled-coil dimerization domains. The coiled-coil dimerization domains may be inserted into the N-terminus and C-terminus of the target protein.

The step of engineering may further include contacting a host with an expression construct. The expression construct may include any one of the engineered nucleic acids described herein. The expression construct may be inserted in a transformation vector. The transformation vector may be used to transform the host. The transformation may be but is not limited to an *Agrobacterium*-mediated transformation, electroporation with a plasmid DNA, a DNA uptake, a biolistic transformation, a virus-mediated transformation, or a protoplast transformation. The transformation may be any other transformation procedure suitable for a particular host. The method may include selecting the host cell that includes the engineered nucleic acid and expresses the chimeric protein. The method may include regenerating the host cell into a multicellular organism. The method may include multiplying the host cell to obtain a plurality of the host cells that include the engineered nucleic acid and expresses the chimeric protein. The activity of the target protein may be repressed. The activity of the target protein may be repressed because the dimeric state may inhibit the function of the target protein.

The method may include exposing the chimeric protein to a triggering condition to disrupt interaction of the first dimerization domain and the second dimerization domain and reactivate the activity of the target protein. The triggering condition may be any one of the triggering conditions described herein. The triggering condition may be a triggering temperature. Protein dimerization may be inherently sensitive to temperature change and could be developed to have the desired temperature-induced dissociation-association response using standard protein engineering techniques. Temperature may be used for temperature-controlled regulation of the activity of target proteins. The target proteins may be enzymes. The temperature-controlled disruption of dimerization may be used as a tool to regulate enzyme catalytic activity. Placing dimerization domains into the same or different proteins, catalytic activity of one or more enzymes can be regulated at will through the control of the dimerization domains, resulting in one or more molecular switches or dimmers. Temperature-sensitive dimerization domains may be found in psychrophilic, mesophilic, thermophilic or hyperthermophilic species living in widely different temperature conditions. These organisms may be used as rich sources of dimerization domains with inherently different temperature responses. Native or synthetic dimerization domains, including homo and heterodimers, irrespective to their size, composition, and affinity may be potentially be tailored to respond to a specific temperature. Temperature-sensitive dimerization domains may be used to link different target proteins into a single, temperature-regulated enzyme complex, or to create heat-inducible homo-oligomers. The protein linking by dimerization domains described may be different from the classic protein fusion where two or more proteins are covalently joined with a long linker that structurally, energetically and functionally uncouple the fused domains (Cutler et al., 2009). To achieve dimerization-driven control of activity through temperature, the temperature-inducible dimerization domains may be placed such that they elicit conformational strain, enforce disfavored orientations, or couple the component enzymes to an enzymatically dysfunctional unit. This method may support assembly of a set of enzymes into a post-translationally co-regulated and temperature-inducible unit, and extend the utility of dimerization-based temperature regulation to a large group of proteins that may not be easily regulated by other means. If needed, sequential activation may be achieved by adjusting melting temperatures of the various dimerization domains to different temperatures.

In an embodiment, temperature-sensitive dimerization domains may be inserted into self-splicing inteins and may be used to control intein switches in heat-inducible regulation of enzyme activity. Inteins may catalyze their own removal from their target protein and covalently join flanking protein sequences by traceless splicing. They may be developed as inducible molecular switches, where insertion of the intein may inhibit and splicing may induce enzyme activity (Shen et al. 2012). Previously developed heat-inducible intein switches are often leaky; inhibition is slowly lost over time. In applications where long-term stability of the switch is desirable, additional temperature regulation through dimerization domains in the intein may provide the necessary control. Heat leads to disruption of the dimer followed by intein splicing. Since intein splicing irreversibly removes the regulatory dimerization domain from the target protein, this switch may be irreversible in contrast to the reversible switches of that are permanently addition to one or more target proteins. Potential sites for dimerization domain insertion may be between the splicing domains at the site where bifunctional inteins have a homing endonuclease domain. That domain may be replaced without disrupting splicing (Ramsden et al., 2011). Small mono-functional inteins without homing endonuclease domains may also be functionalized by insertion into a similar position between their splicing domains. Each of the two dimerization domains may be placed into the same intein. Alternatively, one domain may be inserted in the intein and the other in the host protein, making dimerization intermolecular.

In an embodiment, interaction of the first dimerization domain and the second dimerization domain may enhance the activity of the target protein. The interaction between the first dimerization domain and the second dimerization domain may be capable of being disrupted upon exposure of the chimeric protein to a triggering condition, and disruption of the interaction disrupts the enhanced activity of the target protein. The triggering condition may be any one of the triggering conditions described herein. Insertion of intra- or intermolecular dimerization domains may also lead to changes in protein stability. Interacting domains with a tendency to aggregate may lead to directed aggregation. Alternately, dimer formation may stabilize the fold of the target protein. Stabilizing the fold of the protein may allow the target protein to be active at temperatures above its typical melting temperature. The enhanced activity may be thermostability. Because temperature-dependent disruption of dimerization is often reversible, control of enzyme activity by dimerization may also be reversible. A dimer may be designed to act as a molecular thermometer to repress or activate enzyme activity within a narrow temperature range.

In an embodiment, a method of regulating the activity of a target protein is provided. The method includes providing a chimeric protein that includes a target protein, a first dimerization domain, a second dimerization domain. The first dimerization domain may be fused to the target protein. The second dimerization domain may be fused to the target protein. The first dimerization domain may interact with the second dimerization domain to alter the activity of the target protein. The first dimerization domain may be selected from the group consisting of: a coiled-coil dimerization domain GCN4, ATF6, CREB1, C/EBPα, Fos, Jun, influenza hemagglutinin, and HIVgp41. The second dimerization domain may be selected from the group consisting of: a coiled-coil dimerization domain GCN4, ATF6, CREB1, C/EBPα, Fos, Jun, influenza hemagglutinin, and HIVgp41. The step of providing may include expressing the chimeric protein in a host. The host may be any host described herein. The activity of the target protein may be repressed. The method may include exposing the host to a triggering condition to disrupt interaction of the first dimerization domain and the second dimerization domain and reactivate the activity of the target protein. The activity of the target protein may be enhanced. The method may include exposing the host to a triggering condition to disrupt interaction of the first dimerization domain and the second dimerization domain and disrupt the activity of the target protein. The triggering condition may be any one of the triggering conditions described herein.

In an embodiment, a method of regulating the activity of a target protein is provided. The method may include providing an engineered nucleic acid encoding a chimeric protein that includes a target protein, a first dimerization domain, a second dimerization domain. The first dimerization domain may be fused to the target protein. The second dimerization domain may be fused to the target protein. The first dimerization domain may interact with the second dimerization domain to alter the activity of the target protein. The first dimerization domain may be selected from the group consisting of: a coiled-coil dimerization domain GCN4, ATF6, CREB1, C/EBPα, Fos, Jun, influenza hemagglutinin, and HIVgp41. The second dimerization domain may be selected from the group consisting of: a coiled-coil dimerization domain GCN4, ATF6, CREB1, C/EBPα, Fos, Jun, influenza hemagglutinin, and HIVgp41. The method may include expressing the engineered nucleic acid in a host to produce the chimeric protein. The method may include exposing the host to a triggering condition. The triggering condition may be any one of the triggering conditions described herein.

In an embodiment, the host may be a plant genetically engineered to include any one of the chimeric proteins described herein. The chimeric protein may include a target protein that is repressed due to interaction between the first dimerization domain and the second dimerization domain. The genetically engineered plants may be harvested and exposed to one or more triggering conditions that disrupts the interaction between the first dimerization domain and the second dimerization domain, and reactivates the activity of the target protein. The genetically engineered plants may be mixed with other substrates. The other substrates may include non-genetically engineered plants.

The genetically engineered plants may be used in methods and processes as substrates for production of fuel. Fuel may include but not limited to ethanol, methanol, propanol, propane, methane or octane. The genetically engineered plants may be used as substrates for productions of chemicals. Chemicals may include but not limited to glucose or other hexoses, pentoses, propane diols, lactic acid, ethanol, ethene, ethane, ethylene, phenolic compounds, amino acids, paper pulp, pesticides, insecticides, other alcohols, or other ethers. The genetically engineered plant may be used for food production. The genetically engineered plant may be used as substrates for production of food additives. The food additives may include but not limited to sugars, vitamins amino acids, sugars, vitamins, or fiber. The food additives may include animal feed. The genetically engineered plant may be used as substrates for production of therapeutic proteins. The therapeutic proteins may include but not limited to hormones, growth factors, or therapeutic antibodies.

The following list includes particular embodiments of the present invention. But the list is not limiting and does not exclude alternate embodiments, as would be appreciated by one of ordinary skill in the art.

Embodiments

1. A chimeric protein comprising a target protein, a first dimerization domain and a second dimerization domain; wherein the first dimerization domain is fused to the target protein, the second dimerization domain is fused to the target protein, the first dimerization domain interacts with the second dimerization domain to alter the activity of the target protein, the first dimerization domain is selected from the group consisting of: a coiled-coil dimerization domain GCN4, ATF6, CREB1, C/EBPα, Fos, Jun, influenza hemagglutinin, and HIVgp41, and the second dimerization domain is selected from the group consisting of: a coiled-coil dimerization domain GCN4, ATF6, CREB1, C/EBPα, Fos, Jun, influenza hemagglutinin, and HIVgp41.

2. The chimeric protein of embodiment 1, wherein the target protein is selected from the group consisting of: a transcription factor, a membrane channel, a membrane transporter, an antibody, a hormonal protein, a mannanase, an amylase, a xylanase, a cellulase, a protease, a lipase, a kinase, a catalase, and a restriction enzyme.

3. The chimeric protein of embodiment 1, wherein the target protein is an intein.

4. The chimeric protein of embodiment 3, wherein the intein is selected from the group consisting of: Tth, mTth, Psp-pol, Mtu RecA, Sce VMA, Pho-RecA, and Tko_RecA.

5. The chimeric protein of embodiment 1, wherein the target protein is an intein-modified protein.

6. The chimeric protein of any one or more of the preceding embodiments, wherein the first dimerization domain, or the second dimerization domain is fused to the N-terminus or the C-terminus of the target protein.

7. The chimeric protein of embodiment 6 further comprising a linker contiguous with and between the first dimerization domain and the target protein, and a second linker contiguous with and between the second dimerization domain and the target protein.

8. The chimeric protein of any one or more of the preceding embodiments, wherein the N-terminus of the second dimerization domain is linked to and contiguous with the C-terminus of the target protein.

9. The chimeric protein of any one more of the embodiments 1-7, wherein the C-terminus of the first dimerization is linked to and contiguous with the N-terminus of the target protein, and the N-terminus of the second dimerization domain is linked to and contiguous with the C-terminus of the target protein.

10. The chimeric protein of any one or more of embodiments 1-5, wherein at least one of the first dimerization domain, or the second dimerization domain is fused to the target protein internally.

11. The chimeric protein of any one or more of the preceding embodiments, wherein the activity of the target protein is repressed, and the interaction between the first dimerization domain and the second dimerization domain is capable of being disrupted upon exposure of the chimeric protein to a triggering condition, and disruption of the interaction reactivates the activity of the target protein.

12. The chimeric protein of embodiment 11, wherein the triggering condition is selected from the group consisting of: a triggering temperature, a triggering pH, a triggering ligand binding, a triggering light, a triggering ion, a triggering sound, and a triggering concentration of a compound.

13. The chimeric protein of any one or more of embodiments 1-10, wherein the activity of the target protein is enhanced, and the interaction between the first dimerization domain and the second dimerization domain is capable of being disrupted upon exposure of the chimeric protein to a triggering condition, and disruption of the interaction disrupts the enhanced activity of the target protein.

14. The chimeric protein of embodiment 13, wherein the enhanced activity is thermostability.

15. The chimeric protein of embodiment 13 or 14, wherein the triggering condition is selected from the group consisting of: a triggering temperature, a triggering pH, a triggering ligand binding, a triggering light, a triggering ion, a triggering sound, and a triggering concentration of a compound.

16. The chimeric protein any one or more of the embodiments 1-2 and 6-12, wherein the target protein includes an amino acid sequence having at least 90% identity to a sequence selected from SEQ ID NO: 1 [O43 T] or SEQ ID NO: 14 [BD25243].

17. The chimeric protein of any one or more of the preceding embodiments, wherein at least one of the first dimerization domain, or the second dimerization domain is included in an amino acid sequence having at least 90% identity to SEQ ID NO: 2[GCN4].

18. The chimeric protein of any one or more of embodiments 1-2 and 6-12 comprising a sequence having at least 90% identity to a reference sequence selected from the group consisting of: SEQ ID NO: 3 [CC1], SEQ ID NO: 4 [CC2], SEQ ID NO: 5 [CC17], SEQ ID NO: 6 [CC13], SEQ ID NO: 7[CC14-1], SEQ ID NO: 8[CC14-2], SEQ ID NO: 9 [CC15], SEQ ID NO: 10 [CC22], SEQ ID NO: 11[CC23], SEQ ID NO: 12 [CC24], SEQ ID NO: 13 [CC30], and SEQ ID NO: 15 [BD25CC2].

19. The chimeric protein of any one or more of the preceding embodiments included in a host, wherein the host is selected form the group consisting of a microorganism, a plant cell, a phage, a virus, a mammalian cell, and an insect cell.

20. An engineered nucleic acid encoding a chimeric protein comprising a target protein that includes a first dimerization domain and a second dimerization domain; wherein the first dimerization domain is fused to the target protein, the second dimerization domain is fused to the target protein, the first dimerization domain interacts with the second dimerization domain to alter the activity of the target protein, the first dimerization domain is selected from the group consisting of: a coiled-coil dimerization domain GCN4, ATF6, CREB1, C/EBPα, Fos, Jun, influenza hemagglutinin, and HIVgp41, and the second dimerization domain is selected from the group consisting of: a coiled-coil dimerization domain GCN4, ATF6, CREB1, C/EBPα, Fos, Jun, influenza hemagglutinin, and HIVgp41.

21. The engineered nucleic acid of embodiment 20, wherein the sequence encoding the target protein has at least 90% identity to SEQ ID NO: 16 [O43 T] or SEQ ID NO: 29 [BD25243].

22. The engineered nucleic acid of embodiment 20 or 21, wherein the sequence encoding at least one of the first dimerization domain, or the second dimerization domain, is included in a sequence with at least 90% identity to SEQ ID NO: 17 [GCN4].

23. The engineered nucleic acid of embodiment 20 comprising a sequence having at least 90% identity to a reference sequence selected from the group consisting of: SEQ ID NO: 18[CC1], SEQ ID NO: 19 [CC2], SEQ ID NO: 20 [CC17], SEQ ID NO: 21 [CC13], SEQ ID NO: 22[CC14-1], SEQ ID NO: 23[CC14-2], SEQ ID NO: 24 [CC15], SEQ ID NO: 25 [CC22], SEQ ID NO: 26 [CC23], SEQ ID NO: 27 [CC24], SEQ ID NO: 28 [CC30], and SEQ ID NO: 30 [BD25CC2].

24. A vector comprising the engineered nucleic acid of any one of embodiments 20-23.

25. A host comprising the engineered nucleic acid of any one of embodiments 20-23, wherein the host is selected from the group consisting of: a microorganism, a plant cell, a phage, a virus, a mammalian cell, and an insect cell.

26. A method of regulating the activity of a target protein comprising engineering a chimeric protein that includes a target protein, a first dimerization domain, a second dimerization domain; wherein the first dimerization domain is fused to the target protein, the second dimerization domain is fused to the target protein, the first dimerization domain interacts with the second dimerization domain to alter the activity of the target protein, the first dimerization domain is selected from the group consisting of: a coiled-coil dimerization domain GCN4, ATF6, CREB1, C/EBPα, Fos, Jun, influenza hemagglutinin, and HIVgp41, and the second dimerization domain is selected from the group consisting of: a coiled-coil dimerization domain GCN4, ATF6, CREB1, C/EBPα, Fos, Jun, influenza hemagglutinin, and HIVgp41.

27. The method of embodiment 26, wherein the step of engineering comprises making an expression construct that includes a nucleic acid encoding the chimeric protein.

28. The method of embodiment 26, wherein the step of making the expression construct includes analyzing an amino acid sequence of the target protein for functionally active regions based on proximity to structures selected from the group consisting of: disulfide bridges, catalytic domains, ligand binding domains, and sites accessible to solvents.

29. The method of embodiment 28 further comprising inserting a nucleic acid that encodes the first dimerization domain, or the second dimerization domain in the nucleic acid encoding the target protein in such a position that effects interaction of the domains and alters the activity of the target protein.

30. The method of embodiment 26, wherein the step of engineering further comprises contacting a host with an expression construct.

31. The method of embodiment 30 further comprising selecting the host expressing the chimeric protein.

32. The method of any one or more of embodiments 26-31, wherein the activity of the target protein is repressed.

33. The method of embodiment 32 comprising exposing the chimeric protein to a triggering condition to disrupt interaction of the first dimerization domain and the second dimerization domain and reactivate the activity of the target protein.

34. The method of embodiment 33, wherein the triggering condition is selected from the group consisting of: a triggering temperature, a triggering pH, a triggering ligand binding, a triggering light, a triggering ion, a triggering sound, and a triggering concentration of a compound.

35. The method of any one or more of embodiments 26-31, wherein the activity of the target protein is enhanced.

36. The method of embodiment 35, wherein the enhanced activity is thermostability.

37. A method of regulating the activity of a target protein comprising providing a chimeric protein that includes a target protein, a first dimerization domain, a second dimerization domain; wherein the first dimerization domain is fused to the target protein, the second dimerization domain is fused to the target protein, the first dimerization domain interacts with the second dimerization domain to alter the activity of the target protein, the first dimerization domain is selected from the group consisting of: a coiled-coil dimerization domain GCN4, ATF6, CREB1, C/EBPα, Fos, Jun, influenza hemagglutinin, and HIVgp41, and the second dimerization domain is selected from the group consisting of: a coiled-coil dimerization domain GCN4, ATF6, CREB1, C/EBPα, Fos, Jun, influenza hemagglutinin, and HIVgp41.

38. The method of embodiment 37, wherein the step of providing comprises expressing the chimeric protein in a host, wherein the host is selected from the group consisting of: a microorganism, a plant cell, a phage, a virus, a mammalian cell, and an insect cell.

39. The method of embodiment 37 or 38, wherein the activity of the target protein is repressed.

40. The method of embodiment 39 comprising exposing the host to a triggering condition to disrupt interaction of the first dimerization domain and thesecond dimerization domain and reactivate the activity of the target protein.

41. The method of embodiment 40, wherein the triggering condition is selected from the group consisting of: a triggering temperature, a triggering pH, a triggering ligand binding, a triggering light, a triggering ion, a triggering sound, and a triggering concentration of a compound.

42. The method of embodiment 41, wherein the triggering condition is a triggering temperature, and the triggering temperature is a temperature higher or equal to 30° C.

43. The method of embodiment 41 or 42, wherein the temperature is 50° C.

44. The method of embodiment 37 or 38, wherein the activity of the target protein is enhanced.

45. A method of regulating the activity of a target protein comprising:

providing an engineered nucleic acid encoding a chimeric protein that includes a target protein, a first dimerization domain, a second dimerization domain; wherein the first dimerization domain is fused to the target protein, the second dimerization domain is fused to the target protein, the first dimerization domain interacts with the second dimerization domain to alter the activity of the target protein, the first dimerization domain is selected from the group consisting of: a coiled-coil dimerization domain GCN4, ATF6, CREB1, C/EBPα, Fos, Jun, influenza hemagglutinin, and HIVgp41, and the second dimerization domain is selected from the group consisting of: a coiled-coil dimerization domain GCN4, ATF6, CREB1, C/EBPα, Fos, Jun, influenza hemagglutinin, and HIVgp41;

expressing the engineered nucleic acid in a host to produce the chimeric protein; and exposing the host to a triggering condition.

46. The method of embodiment 45, wherein the triggering condition is selected from the group consisting of: a triggering temperature, a triggering pH, a triggering ligand binding, a triggering light, a triggering ion, a triggering sound, and a triggering concentration of a compound.

47. A method of regulating the activity of a target protein within a chimeric protein that includes the target protein, a first dimerization domain fused to the target protein, and a second dimerization domain fused to the target protein, where the first dimerization domain interacts with the second dimerization domain to alter the activity of the target protein, the method comprising exposing the chimeric protein to a triggering condition to disrupt interaction of the first dimerization domain and the second dimerization domain, wherein the first dimerization domain is selected from the group consisting of: a coiled-coil dimerization domain GCN4, ATF6, CREB1, C/EBPα, Fos, Jun, influenza hemagglutinin, and HIVgp41, and the second dimerization domain is selected from the group consisting of: a coiled-coil dimerization domain GCN4, ATF6, CREB1, C/EBPα, Fos, Jun, influenza hemagglutinin, and HIVgp41.

48. The method of embodiment 47, wherein the chimeric protein is within a host selected from the group consisting of: a microorganism, a plant cell, a phage, a virus, a mammalian cell, and an insect cell.

49. The method of any one of embodiments 47-48, wherein the chimeric protein is encoded by an engineered nucleic acid and the method further comprises further comprising expressing the chimeric protein from the engineered nucleic acid.

50. The method of any one of embodiments 47-49, wherein the triggering condition is selected from the group consisting of: a triggering temperature, a triggering pH, a triggering ligand binding, a triggering light, a triggering ion, a triggering sound, and a triggering concentration of a compound.

51. The method of any one of embodiments 47-50, wherein the triggering condition is a triggering temperature, and the triggering temperature is a temperature higher or equal to 30° C.

52. The method of embodiment 51, wherein the temperature is 50° C.

53. The method of any one of embodiments 47-52, wherein the activity of the target protein is repressed prior to exposing the chimeric protein to the triggering condition.

54. The method of any one of claims 47-53, wherein the activity of the target protein is enhanced after exposing the chimeric protein to the triggering condition.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1

Experimental Overview

The following non-limiting example demonstrates dimerization domain-dependent thermal regulation of enzyme activity in several proof of concept experiments. The method to regulate enzyme activity by intramolecular coiled-coil dimerization is provided.

A general strategy for engineering temperature regulated dimerization domains to regulate enzyme activity may include 5 or more steps: 1) Select dimerization domains for temperature sensitivity. 2) Select insertion points. 3) Select linkers to connect the host sequences to the dimerization domains. 4) Express the chimeric enzyme in *Escherichia coli* or another suitable host to test activity at a range of temperatures. 5) Modify the enzyme through targeted mutagenesis and test activity at a range of temperatures. This strategy is outlined for a single domain enzyme of the GH11 family, the xylanase O43T [SEQ ID NO: 1] (Schlacher et al. 1996), and a two domain enzyme containing a domain of the GH5 family, BD25243 [SEQ ID NO: 14] (Thatcher L F et al. 2012). The single domain enzyme is regulated by N- and C-terminal dimerization domain, while in the two domain enzyme one of the dimerization domain is located within the protein sequence and the other C-terminally attached.

Example 2

Selection of Dimerization Domains for Temperature Sensitivity

A suitable dimerization domain for the development of a switch would be both well-studied and small. Previous experimental studies of a dimerization domain can guide rational mutagenesis of the domain. Small domains are more easily modeled and have a smaller number of positions where mutations must be considered.

Coiled-coils are small dimerization domains that have been well-studied in the literature (Burkhard et al. 2001). The coiled-coil dimerization domain of the GCN4 protein [SEQ ID NO: 2] from *Saccharomyces cerevisiae* is particularly well-studied (Harbury et al. 1993). Modifications to GCN4 are known that increase and decrease the temperature at which the domains no longer dimerize (Bunagan et al. 2006, O'Shea et al. 1993, Spek et al. 1998, Zitzewitz et al. 2000), and the three dimensional structure is well-described (O'Shea et al. 1991, Ellenberger et al. 1992).

Dimerization domains are not limited to coil-coils. Any dimerization domain may be used for development of a switch.

Example 3

Control of the Activity of the Hydrolytic Enzyme O43T: Selection of Insertion Points in O43T The N-terminus and C-terminus of the water soluble domain of O43T are separated by a distance of approximately 3.8 nm (Gruber et al. 1998), a distance similar to the 3.6 nm that separates the N-terminus and C-terminus of the region of GCN4 required for dimerization (Ellenberger et al. 1992). The N-terminus and C-terminus of O43T are also on the opposite face of the enzyme from the active site, decreasing the potential impact of monomeric states of dimerization domains on the enzymatic activity of O43T.

GCN4 forms a parallel dimeric structure, placing both N-termini on the same side and both C-termini on the same side. Placing one domain in frame before the N-terminus of O43T and one domain in frame after the C-terminus of O43T allows the two N-termini (and C-termini) of the dimerization domains to be on the same side, as required for parallel dimerization. Modeling of insertion sites relies on molecular modeling techniques such as molecular dynamics simulations and protein design calculations.

Example 4

Selection of Linkers to Connect the O43T to the Dimerization Domains

Given that the termini of the required region GCN4 are closer than those in O43T, short peptide linkers may be necessary for dimerization in the context of O43T. Peptide linkers that are too long, because they would constrain portions of the enzyme weakly, would likely make enzyme activity less dependent on dimerization.

Protein modeling was used to select minimal length linkers to connect O43T to the GCN4 dimerization domains. The protein sequence of the linkers was initially taken from the amino acid sequence adjoining the dimerization domains of GCN4 in the wild-type GCN4 protein. Different length linkers were used to connect the structures of O43T (Gruber et al. 1998) and GCN4 (Ellenberger et al. 1992). Initial models were subjected to short (5 ns) molecular dynamics simulations of the protein model in a water box using the program NAMD (Phillips et al. 2005). The selected linkers (Glu-Arg at the O43T N-terminus and Gln at the C-terminus) were chosen because they bring the GCN4 domains close to the O43T structure without disrupting either structure during the simulation.

Example 5

Figure 2:
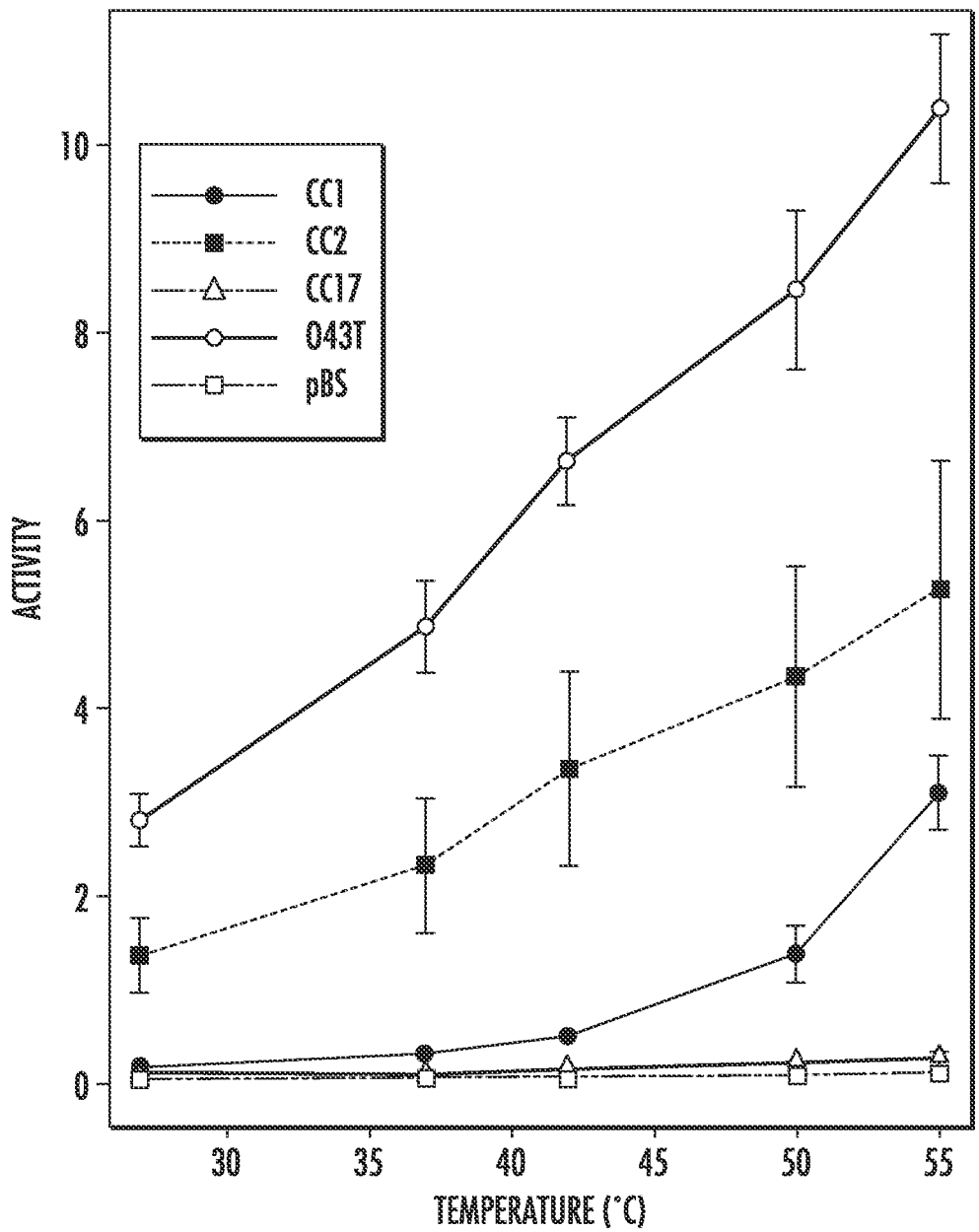
FIG. 2 illustrates enzyme activity of a chimeric protein O43T-GCN4 (CC1) and two GCN4 variants (CC2 and CC17).

Expression of the Chimeric Enzyme in *Escherichia coli* and Test Activity at a Range of Temperatures The initial construct, CC-1 [SEQ ID NO: 3], was codon optimized and placed into a pBS vector. The vector was transformed into *Escherichia coli* cells and expression induced by auto-induction media. Lysed cell extract was then tested for the ability to release dye from Birchwood AZCL-xylan during a 30 minute incubation at a range of temperatures. FIG. 2 illustrates that the activity of CC-1 containing extract increases significantly with temperature, as desired.

The chimeric enzyme may be expressed in any compatible expression host. A host may be a microorganism. The microorganism may be but is not limited to *Escherichia coli, Saccharomyces* ssp., *S. cerevisiae, Pichia* ssp., and *P. pastoris Bacillus subtilus* and others known in the art. A host may be a cell. The cell may be a microbial cell, a fungal cell, a mammalian cell, a plant cell or an insect cell. A host may be a phage or a virus.

The expression cassette may encode an intein-modified protein. The intein-modified protein may include a target protein or part thereof and an intein thereof fused either internally or terminally to the target protein or part thereof in such a position as to substantially reduce the activity of the target protein or part thereof. The intein may be capable of effecting trans- or cis-splicing of the modified protein. The target protein may regain activity following trans- or cis-splicing of the modified protein.

Example 6

Modification of the Enzyme Through Targeted Mutagenesis and Test Activity at a Range of Temperatures To improve on the initial CC-1 construct, targeted mutagenesis was used to change the activity profile of the chimeric enzyme. Birchwood AZCL-xylan substrate was added to cell lysates containing variants of O43T-GCN4 and heated to various temperatures in 384 well plates. After 30 minutes the absorbance at 590 nm measured. CC1 is the initial design, while CC2 [SEQ ID NO: 4] is a variant that destabilizes the GCN4 coiled coil and CC17 [SEQ ID NO: 5] is a variant that stabilizes the GCN4 coiled coil. O43T is the parent enzyme, while pBS marks a cell lysate where an empty vector was transformed. FIG. 2 illustrates enzyme activity of a chimeric protein O43T-GCN4 (CC1) and two GCN4 variants (CC2 and CC17). As shown in this figure, a strongly stabilizing set of targeted mutations to GCN4 including eight Val to Ile mutations completely silenced O43T activity (CC17) while a strongly destabilizing set of mutations to GCN4 such as the eight mutations to Gly lead to higher low temperature activity (CC2).

Figure 3:
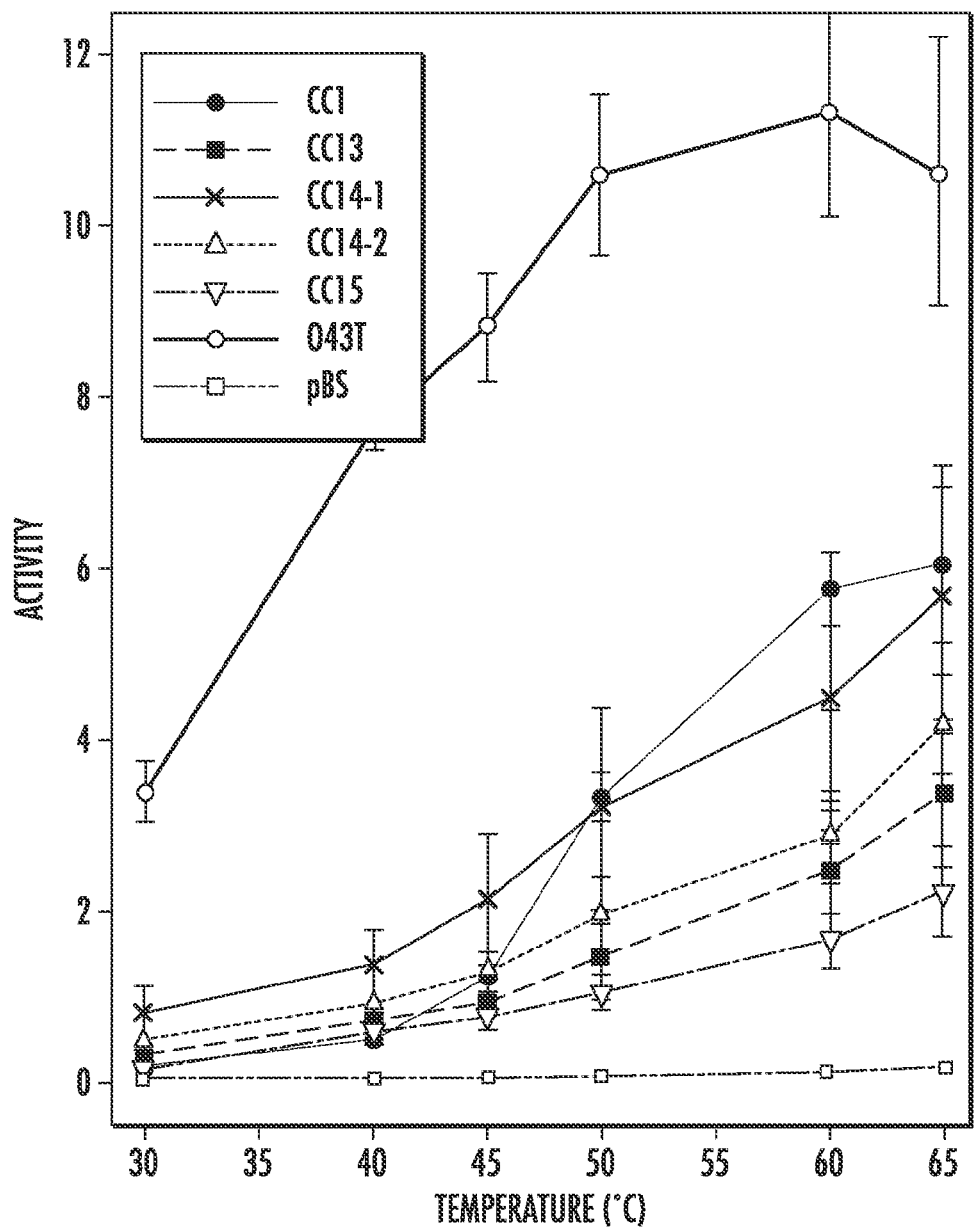
FIG. 3 illustrates enzyme activity of O43T-GCN4 variants with shorter linkers (CC13, CC14-1, CC14-2 and CC15).
Figure 4:
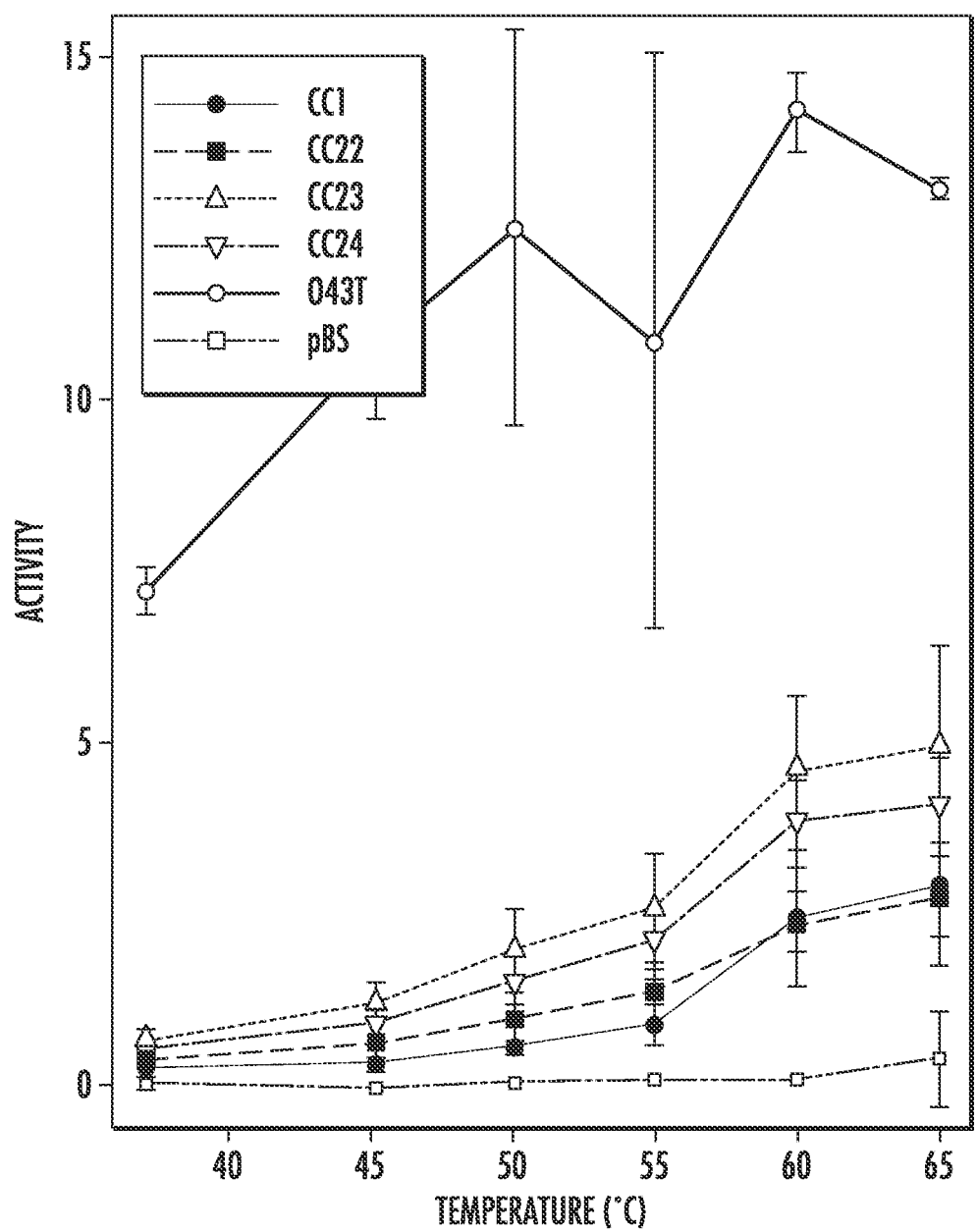
FIG. 4 illustrates enzyme activity of O43T-GCN4 variants with longer linkers (CC22, CC23 and CC24).

FIG. 3 illustrates enzyme activity of O43T-GCN4 variants with shorter linkers using the birchwood AZCL-xylan assay. Referring to FIG. 3, CC1 [SEQ ID NO: 3] is the initial design, CC13 [SEQ ID NO: 6], CC14-1 [SEQ ID NO: 7], CC14-2 [SEQ ID NO: 8], and CC15 [SEQ ID NO: 9] are variants with shorter linkers between O43T and the GCN4 dimerization domains, O43T is the parent enzyme, and pBS marks a cell lysate where an empty vector was transformed. FIG. 4 illustrates enzyme activity of O43T-GCN4 variants with longer linkers using the birchwood AZCL-xylan assay of O43T-GCN4. Referring to this figure, CC1 [SEQ ID NO: 3] is the initial design, CC22 [SEQ ID NO: 10], CC23 [SEQ ID NO: 11], and CC24 [SEQ ID NO: 12] are variants with longer linkers between O43T and the GCN4 dimerization domains, O43T is the parent enzyme, and pBS marks a cell lysate where an empty vector was transformed. Referring to FIG. 3 and FIG. 4, shortening (FIG. 3) or lengthening (FIG. 4) the linkers by one to three amino acid residues between O43T and the dimerization domains both led to decreased suppression of low temperature activity.

Figure 5:
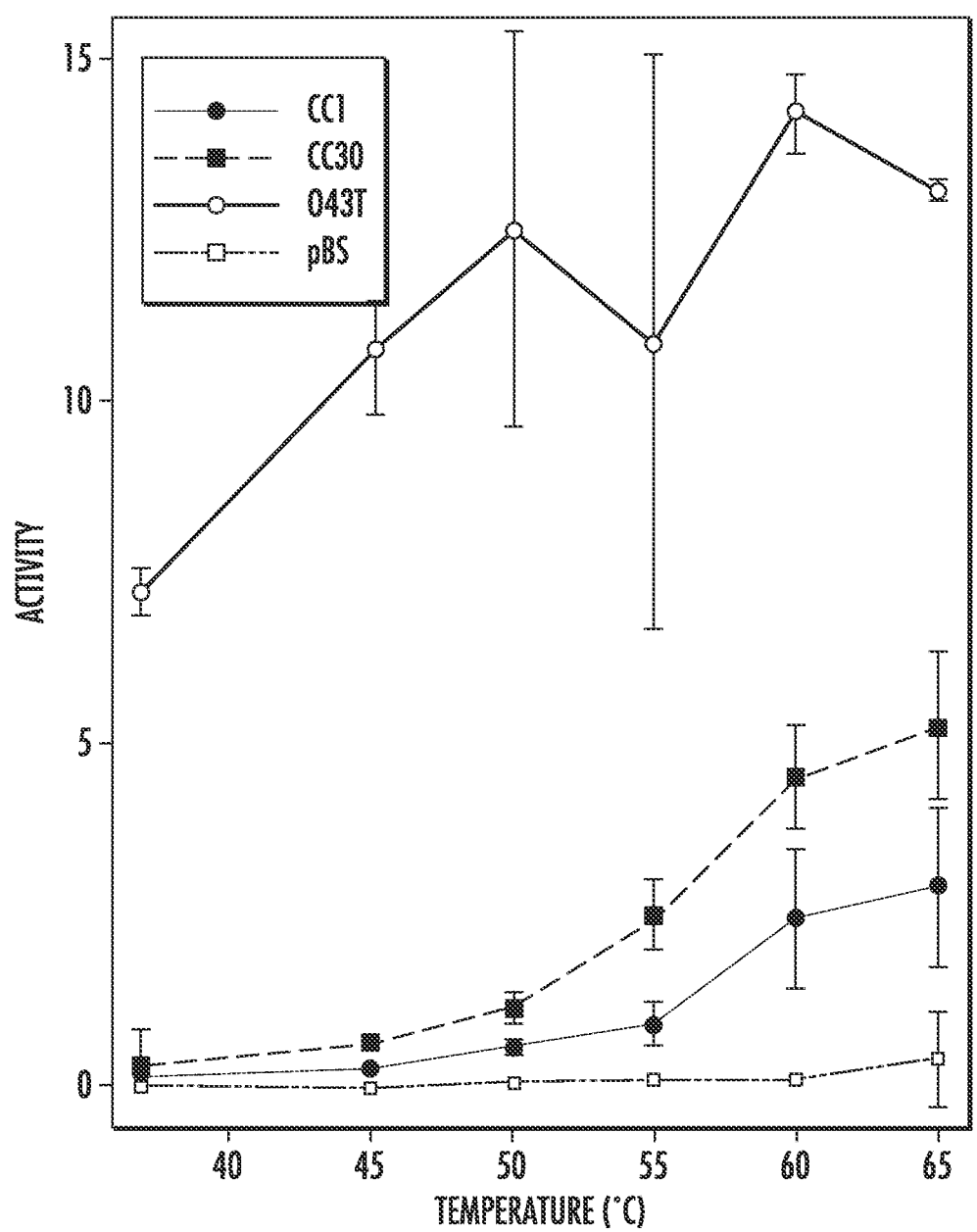
FIG. 5 illustrates enzyme activity of an improved O43T-GCN4 (CC30) variant.

A point mutation (E33T) in the N-terminal linker was selected for further development as it significantly increased the high temperature activity of the enzyme in CC30 [SEQ ID NO: 13] without greatly increasing the low temperature activity. FIG. 5 illustrates enzyme activity of an improved O43T-GCN4 variant using the birchwood AZCL-xylan assay. As shown in this figure, CC1 [SEQ ID NO: 3] is the initial design, CC30 [SEQ ID NO: 13] is a variant with similar low temperature activity but higher high temperature activity, O43T is the parent enzyme, and pBS marks a cell lysate where an empty vector was transformed.

Example 7

Control of the Activity of the Hydrolytic Enzyme BD25243. Selection of Dimerization Domains for Temperature Sensitivity Given the success of regulating O43T activity with the GCN4 coiled coil dimerization domain, the identical domain was selected for BD25243 [SEQ ID NO: 14].

Example 8

Selection of Insertion Points in BD25243 Selection of Insertion Points in BD25243

BD25243 contains two domains: a cellulose binding domain (CBD) followed by a cellulase domain (GH5). To limit cellulase activity, the GH5 domain was targeted. A homology model of the GH5 domain was constructed based on the structure of EG1 from *Thermoascus aurantiacus* (Lo Leggio 2002) given the 63% sequence identity of the two domains.

The N-terminal GCN4 domain was inserted within the wild-type linker connecting the CBD and GH5 domains, while the C-terminal GCN4 domain was inserted at the C-terminus of BD25243. As was the case for O43T, the dimerization domains are on the opposite face of the enzyme from the GH5 active site, potentially decreasing the effect of the monomeric states of the dimerization domains on BD25243 enzyme activity. Because the N-terminal insertion is in the flexible linker between the CBD and GH5 domains, the insertion should have a minimal impact on structural stability of BD25243.

Example 10

Selection of Linkers to Connect BD25243 to the Dimerization Domains

Based on the homology model, the N-terminus of the GH5 domain (contained in the linker between the CBD and GH5 domains) and the C-terminus of BD25243 are separated by approximately 1.0 nm. Because this distance is shorter than the distance between the N-terminus and C-terminus of GCN4 (Ellenberger et al. 1992), protein modeling was used to select minimal length linkers that would allow BD25243 to accommodate the structure of GCN4. The N-terminal linker sequence was taken from linker between the CBD and GH5 domains while the C-terminal linker sequence was taken from wild-type GCN4.

Example 11

Figure 6:
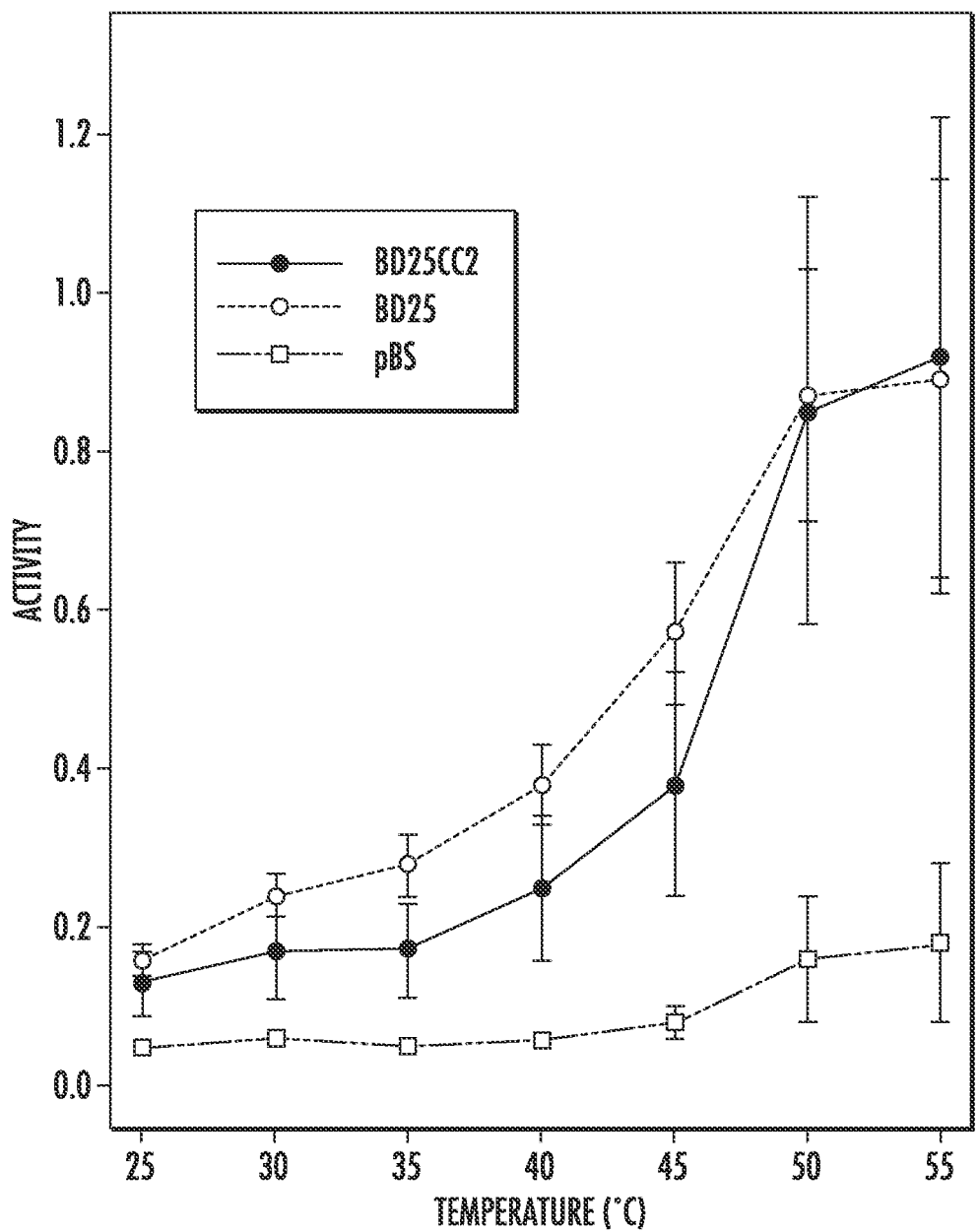
FIG. 6 illustrates enzyme activity of a BD25243-GCN4 variant (BD25CC2) assessed by AZCL-HE-Cellulose assay. BD25 is the parent BD25243 enzyme, while pBS marks a cell lysate where an empty vector was transformed.

Expression of the Chimeric Enzyme in *Escherichia coli* and Test Activity at a Range of Temperatures The initial construct, BD25CC2, was codon optimized and placed into a pBS vector. The vector was transformed into *Escherichia coli* cells and expression induced by auto-induction media. Lysed cell extract was then tested for its ability to release dye from AZCL-HE-Cellulose during 3 hour incubation at a range of temperatures. The activity of the BD25CC2 [SEQ ID NO: 15] is decreases at low temperatures relative to BD25243, as desired. FIG. 6 illustrates enzyme activity of an initial BD25243-GCN4 variants using AZCL-HE-Cellulose assay. As shown in FIG. 6, BD25CC2 is the initial design, BD25 is the parent BD25243 enzyme, and pBS marks a cell lysate where an empty vector was transformed.

Example 12

Control of the Activity of the Enzyme is Retained when Expressed in Plant Tissues To test whether the O43T-GCN4 variant retained its differential activation at low and high temperatures, the O43T-GCN4 variant CC30 [SEQ ID NO: 13] was expressed in maize under the control of a leaf-specific promoter. Transgenic plants expressing this enzyme were grown to maturity, allowed to senesce naturally, and then the senescent plant material (stover) was oven-dried (37° C.) and milled to a fine powder. 500 µl of extraction buffer (100 mM sodium phosphate buffer, pH 6.5) was added to 20 mg stover samples from each of three separate transgenic lines that express this enzyme as well as a fourth control line that does not express this enzyme. These mixtures were incubated at 55° C. for 60 minutes with gentle agitation. Subsequently, the samples were centrifuged briefly, and the supernatants (extracts) were removed and assayed for enzyme activity.

Figure 7:
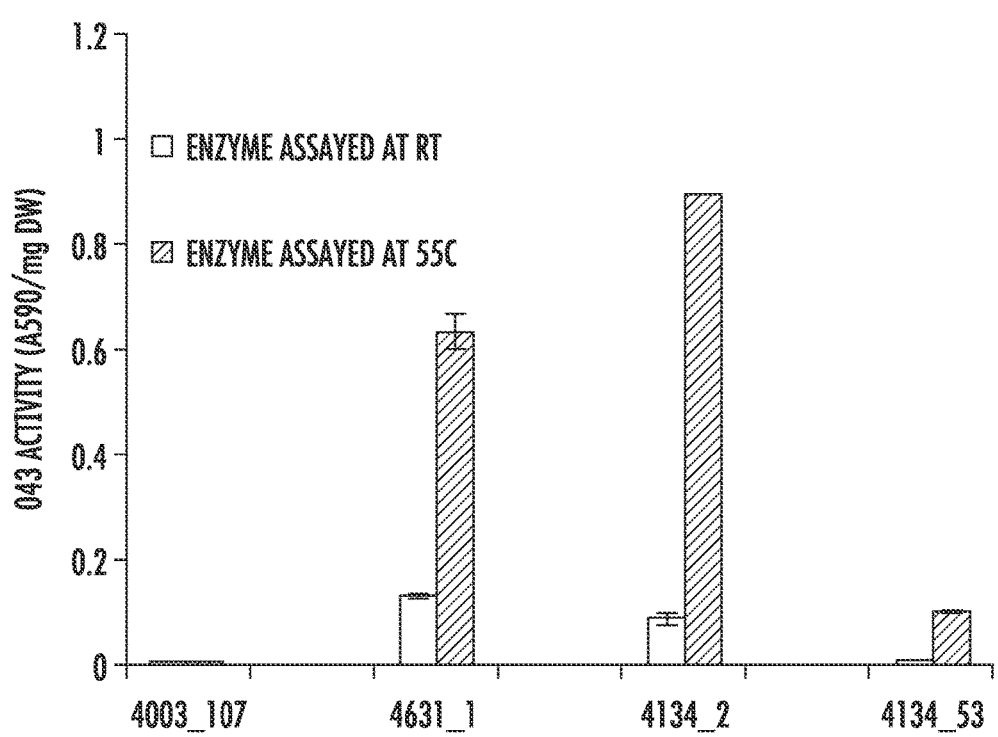
FIG. 7 illustrates xylanase activity of the plant-expressed O43T-GCN4 variant CC30.

To assay activity of the O43-GCN4 variant CC30, 50 µl of extract was mixed with 450 µl of assay buffer (100 mM sodium phosphate buffer, pH 6.5). Subsequently, one Xylazyme AX pellet (Megazyme, Wicklow, Ireland) was added to each sample and incubated at either 37° C. or 55° C. for 60 minutes. Then, 1000 µl of 2% Tris base was added to each sample to stop the reaction. Again, the samples were centrifuged to clarify the supernatant, and the absorbance at 590 nm was determined for each supernatant. FIG. 7 illustrates xylanase activity of the plant-expressed O43T-GCN4 variant CC30. Stover samples were collected for three transgenic lines that express the enzyme: 4631_1, 4134_2, and 4134_53. The stover sample 4003_107 was collected from a control line that does not express the enzyme. It was observed that stover samples extracted from the transgenic maize plants, the O43T-GCN4 variant CC30 showed an activity profile that was similar to that of the enzyme expressed in *E. coli*. It was also observed, that at 55° C., the enzyme had 4- to 10-fold higher activity than it had at 37° C.

It is understood, therefore, that this invention is not limited to the particular embodiments disclosed, but is intended to cover all modifications which are within the spirit and scope of the invention as defined by the appended claims; the above description; and/or shown in the attached drawings.

REFERENCES

Amara J, Clackson T, Rivera V M, Guo T, Keenan T, Natesan S, Pollock R, Wuyang, Courage N L, Holt D A and Gilman M (1997) A versatile synthetic dimerizer for the regulation of protein—protein interactions. *Proc. Natl. Acad. Sci. USA* 94:10618-10623.

Armstrong C T, Boyle A L, Bromley E H C, Mahmoud Z N, Smith L, Thomson A R, Woolfson D N (2009) Rational design of peptide-based building blocks for nanoscience and synthetic biology. *Faraday Discuss.* 143: 305-317.

Armstrong C R, Vincent T L, Green P J, Woolfson D N (2011) SCORER 2.0: An algorithm for distinguishing parallel dimeric and trimeric coiled-coil sequences. Bioinformatics 27(14):1908-1914.

Banwell E F, Abelardo E S, Adams D J, Birchall M A, Corrigan A, Donald A M, Kirkland M, Serpell L C, Butler M F, Woolfson D N (2009) Rational design and application of responsive alpha-helical peptide hydrogels. Nat Mater 8: 596-600.

Bromley E H C, Channon K J, King P J S, Mahmoud Z N, Banwell E F, Butler M F, Crump M P, Dafforn T E, Hicks D M R, Hirst J D, Rodger A and Woolfson D N (2010) Assembly Pathway of a Designed alpha-Helical Protein Fiber. Biophysical Journal 98(8), 1668-1676.

Brown J H, 2006, "Breaking symmetry in protein dimers: designs and functions," Protein Sci. 15(1): 1-13.

Bunagan M R, Cristian L, DeGrado W F, Gai F (2006) Truncation of a cross-linked GCN4-p1 coiled coil leads to ultrafast folding. *Biochem* 45(36):10981-6.

Burkhard P, Stetefeld J, Strelkov S V (2001) Coiled coils: a highly versatile protein folding motif. *Trends Cell Bio* 11(2):82-88.

Cutler T A, Mills B M, Lubin D J, Chong L T and Loh S N (2009) Effect of Interdomain Linker Length on an Antagonistic Folding-Unfolding Equilibrium between Two Protein Domains. *J Mol Biol.* 386(3): 854-868.

Fletcher D M, Boyle A L, Bruning M, Bartlett G J, Vincent T L, Zaccai N R, Armstrong C T, Bromley E H C, Booth P J, Brady R L, Thomson A R, and Woolfson D N (2012) A Basis Set of de Novo Coiled-Coil Peptide Oligomers for Rational Protein Design and Synthetic Biology. ACS Synthetic Biology 6: 240-250.

Gagné D, Charest L A, Morin S, Kovrigin E L, Doucet N (2012) Conservation of flexible residue clusters among structural and functional enzyme homologues. *J Biol Chem* 287(53):44289-300.

Gray B N, Bougri O, Carlson A R, Meissner J, Pan S, Parker M H, Zhang D, Samoylov V, Ekborg N A, Raab, M R (2011) Global and grain-specific accumulation of glycoside hydrolase family 10 xylanases in transgenic maize (*Zea mays*). *Plant Biotechnol J.* 9(9):1100-8.

Gruber K, Klintschar G, Hayn M, Schllacher A, Steiner W, Kratky C (1998) Thermophilic xylanase from *Thermomyces lanuginosus*: high-resolution X-ray structure and modeling studies. *Biochem* 37(39):13475-85.

Hadley E B, Testa O D, Woolfson D N, Gellman S H (2008) Preferred side-chain constellations at antiparallel coiled-coil interfaces. Proc. Natl. Acad. Sci. U.S.A 105, 530-535, Harbury P B, Zhang T, Kim P S, Alber T (1993) A switch between two-, three-, and four-stranded coiled coils in GCN4 leucine zipper mutants. *Science* 262(5138): 1401-7.

Ellenberger T E, Brandl C J, Struhl K, Harrison S C (1992) The GCN4 basic region leucine zipper binds DNA as a dimer of uninterrupted alpha helices: crystal structure of the protein-DNA complex. *Cell* 71:1223-1237.

Jones S, Thornton J M (1996) Principles of protein-protein interactions. *PNAS* 93(1):13-20.

Landschulz W H, Johnson P F, McKnight S L (1988) The leucine zipper: a hypothetical structure common to a new class of DNA-binding proteins. *Science* 240 (4860): 1759-1764

Lo Leggio L, Larsen S (2002) The 1.62 Å structure of *Thermoascus aurantiacus* endoglucanase: completing the structural picture of subfamilies in glycoside hydrolase family 5. *FEBS Lett* 523(1-3):103-108.

Mason J M, Arndt K M (2004) Coiled coil domains: stability, specificity, and biological implications. Chembiochem 5 (2): 170-176.

Moutevelis E, Woolfson D N (2009) A periodic table of coiled-coil protein structures. Journal of Molecular Biology 385(3): 726-732.

Nagai T, Sawano A, Park E S, Miyawaki A (2001) Circularly permuted green fluorescent proteins engineered to sense Ca2+. *PNAS* 98(6):3197-202.

O'Shea E K, Rutkowski R and Kim P S (1989) Evidence that the leucine zipper is a coiled coil. *Science* 243: 538-542.

O'Shea E K, Klemm J D, Kim P S, Albers T (1991) X-ray structure of the GCN4 leucine zipper, a two-stranded, parallel coiled coil. *Science* 254(5031):539-44.

O'Shea E K, Lumb K J, Kim P S (1993) Peptide 'velcro': design of a heterodimeric coiled coil. *Current Biology* 3(10):658-67.

Phillips J C, Braun R, Wang W, Gumbart J, Tajkhorshid E, Villa E, Chipot C, Skeel R D, Kale L, Schulten K (2005) Scalable molecular dynamics with NAMD. *J Comp Chem* 26(16):1781-802.

Ramsden R, Arms L, Davis T N and Muller E G D (2011) An intein with genetically selectable markers provides a new approach to internally label proteins with GFP. *BMC Biotechnology* (11):71-82.

Russell G L, Britton L N (2002) Use of certain alcohol ethoxylates to maintain protease stability in the presence of anionic surfactants. *J Surfactants and Detergents* 5(1):5-10.

Schlacher A, Holzmann K, Hayn M, Steiner W, Schwab H (1996) Cloning and characterization of the gene for the thermostable xylanase XynA from *Thermomyces lanuginosus*. *J Biotech* 49:211-8.

Stauffer C E, Treptow R S (1973) Inactivation of subtilisin Carlsberg in surfactant and salt solutions. *Biochem et Biophys Acta-Prot Str* 295(2):457-66.

Shen B, Sun X, Zuo X, Shilling T, Apgar J, Ross M, Bougri O, Samoylov V, Parker M, Hancock E, Lucero H, Gray B, Ekborg N A, Zhang D, Johnson J S, Lazar G, Raab M R (2012) Engineering a thermoregulated intein-modified xylanase into maize for consolidated lignocellulosic biomass processing. *Nature Biotech.* 30(11):1131-6.

Spek E J, Bui A H, Lu M, Kallenbach N R (1998) Surface salt bridges stabilize the GCN4 leucine zipper. Prot Sci 7(11):2431-37.

Spencer D M, Wandless T J, Schreiber S L, Crabtree G R (1993) Controlling signal transduction with synthetic ligands. *Science.* 262(5136):1019-24.

Spencer, D. M. (1996) Creating conditional mutations in mammals. Trends Genet. 12: 181-187.

Straussman R, Ben-Ya'acov A, Woolfson D N, and Ravid S (2007) Kinking the coiled coil Å—negatively charged residues at the coiled-coil interface. J Mol Biol 366, 1232-1242.

Testa O D, Moutevelis E, Woolfson D N (2009) CC+: a relational database of coiled-coil structures Nucleic Acid Research, Vol. 37, Database issue, D315-D322.

Thatcher L F, Gardiner D M, Kazan K, Manners J (2012) A highly conserved effector in *Fusarium oxysporum* is required for full virulence on Arabidopsis. *Mol Plant Microbe Interact.* 25:180-190.

Villali J, Kern D (2010) Choreographing an enzyme's dance. *Curr. Op. Chem. Biol.* 14(5):636-43.

Vincent, T L, Green P J, Woolfson D N (2013) LOGI-COIL—Multi-state prediction of coiled-coil oligomeric state. Bioinformatics 29(1):69-76.

Woolfson D N (2005) The design of coiled-coil structures and assemblies. Adv Prot Chem 70, 79-112.

Yu Y B (2002) Coiled-coils: stability, specificity, and drug delivery potential. *Adv Drug Deliv Rev* 54 (8): 1113-1129.

Zhou X X, Chung H K, Lam A J, Lin M Z (2012) Optical control of protein activity by fluorescent protein domains. *Science.* 338(6108):810-4.

Zitzewitz J A, Ibarra-Molero B, Fishel D R, Terry K L, Matthews C R (2000) Preformed secondary structure drives the association reaction of GCN4-p1, a model coiled-coil system. *J Mol Bio.* 296(4):1105-16.

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

What is claimed is:

1. A chimeric protein comprising a target protein fused to a first dimerization domain and a second dimerization domain,
wherein the C-terminus of the first dimerization domain is linked to the N-terminus of the target protein, and the N-terminus of the second dimerization domain is linked to the C-terminus of the target protein, the first dimerization domain interacts with the second dimerization domain and represses the activity of the target protein, the interaction between the first dimerization domain and the second dimerization domain is capable of being disrupted upon exposure of the chimeric protein to a triggering condition, and disruption of the interaction reactivates the activity of the target protein; and
wherein the target protein comprises a GH11 xylanase, each of the first dimerization domain and the second dimerization domain comprises a coiled-coil dimerization domain GCN4, and the triggering condition is an increased temperature.

2. The chimeric protein of claim 1 further comprising a first linker contiguous with and between the first dimerization domain and the target protein, and a second linker contiguous with and between the second dimerization domain and the target protein.

3. The chimeric protein of claim 1, wherein the target protein includes an amino acid sequence having at least 90% identity to the sequence of SEQ ID NO: 1 [O43 T].

4. The chimeric protein of claim 1, wherein a sequence of at least one of the first dimerization domain, or the second dimerization domain is included in an amino acid sequence having at least 90% identity to SEQ ID NO: 2[GCN4].

5. The chimeric protein of claim 1 included in a host, wherein the host is selected form the group consisting of a microorganism, a plant cell, a phage, a virus, a mammalian cell, and an insect cell.

6. An engineered nucleic acid encoding a chimeric protein comprising a target protein fused to a first dimerization domain and a second dimerization domain,
wherein the C-terminus of the first dimerization is linked to the N-terminus of the target protein, and the N-terminus of the second dimerization domain is linked to the C-terminus of the target protein, the first dimerization domain interacts with the second dimerization domain and represses the activity of the target protein, the interaction between the first dimerization domain and the second dimerization domain is capable of being disrupted upon exposure of the chimeric protein to a triggering condition, and disruption of the interaction reactivates the activity of the target protein; and
wherein the target protein comprises a GH11 xylanase, and each of the first dimerization domain and the second dimerization domain comprises coiled-coil dimerization domain GCN4, and the triggering condition is an increased temperature.

7. The engineered nucleic acid of claim 6, wherein the sequence encoding the target protein has at least 90% identity to SEQ ID NO: 16 [O43 T].

8. The engineered nucleic acid of claim 6, wherein the sequence encoding at least one of the first dimerization domain, or the second dimerization domain, is included in a sequence with at least 90% identity to SEQ ID NO: 17[GCN4].

9. A vector comprising the engineered nucleic acid of claim 6.

10. A host comprising the engineered nucleic acid of claim 6, wherein the host is selected from the group consisting of: a microorganism, a plant cell, a phage, a virus, a mammalian cell, and an insect cell.

11. A chimeric protein comprising a sequence having at least 90% identity to a reference sequence selected from the group consisting of: SEQ ID NO: 3 [CC1], SEQ ID NO: 4 [CC2], SEQ ID NO: 5 [CC17], SEQ ID NO: 6[CC13], SEQ ID NO: 7[CC14-1], SEQ ID NO: 8[CC14-2], SEQ ID NO: 9 [CC15], SEQ ID NO: 10 [CC22]., SEQ ID NO: 11[CC23], SEQ ID NO: 12 [CC24], and SEQ ID NO: 13 [CC30], wherein the chimeric protein has a glucohydrolase activity.

12. An engineered nucleic acid encoding a chimeric protein and comprising a sequence having at least 90% identity to a reference sequence selected from the group consisting of: SEQ ID NO: 18[CC1], SEQ ID NO: 19 [CC2], SEQ ID NO: 20 [CC17], SEQ ID NO: 21 [CC13], SEQ ID NO: 22[CC14-1], SEQ ID NO: 23[CC14-2], SEQ ID NO: 24 [CC15], SEQ ID NO: 25 [CC22], SEQ ID NO: 26 [CC23], SEQ ID NO: 27 [CC24], and SEQ ID NO: 28 [CC30], wherein the chimeric protein has a glucohydrolase activity.

* * * * *

SEQUENCE LISTING

<160> NUMBER OF SEQ ID NOS: 30

<210> SEQ ID NO 1
<211> LENGTH: 225
<212> TYPE: PRT
<213> ORGANISM: Artificial Sequence
<220> FEATURE:
<223> OTHER INFORMATION: Synthetic construct, O43T

<400> SEQUENCE: 1

```
Met Val Gly Phe Thr Pro Val Ala Leu Ala Ala Leu Ala Ala Thr Gly
1               5                   10                  15

Ala Leu Ala Phe Pro Ala Gly Asn Ala Thr Glu Leu Glu Lys Arg Gln
                20                  25                  30

Thr Thr Pro Asn Ser Glu Gly Trp His Asp Gly Tyr Tyr Tyr Ser Trp
            35                  40                  45

Trp Ser Asp Gly Gly Ala Gln Ala Thr Tyr Thr Asn Leu Glu Gly Gly
        50                  55                  60

Thr Tyr Glu Ile Ser Trp Gly Asp Gly Gly Asn Leu Val Gly Gly Lys
65                  70                  75                  80

Gly Trp Asn Pro Gly Leu Asn Ala Arg Ala Ile His Phe Glu Gly Val
                85                  90                  95

Tyr Gln Pro Asn Gly Asn Ser Tyr Leu Ala Val Tyr Gly Trp Thr Arg
                100                 105                 110

Asn Pro Leu Val Glu Tyr Tyr Ile Val Glu Asn Phe Gly Thr Tyr Asp
            115                 120                 125

Pro Ser Ser Gly Ala Thr Asp Leu Gly Thr Val Glu Cys Asp Gly Ser
        130                 135                 140

Ile Tyr Arg Leu Gly Lys Thr Thr Arg Val Asn Ala Pro Ser Ile Asp
145                 150                 155                 160

Gly Thr Gln Thr Phe Asp Gln Tyr Trp Ser Val Arg Gln Asp Lys Arg
                165                 170                 175

Thr Ser Gly Thr Val His Thr Gly Cys His Phe Asp Ala Trp Ala Arg
            180                 185                 190

Ala Gly Leu Asn Val Asn Gly Asp His Tyr Tyr Gln Ile Val Ala Thr
        195                 200                 205

Glu Gly Tyr Phe Ser Ser Gly Tyr Ala Arg Ile Thr Val Ala Asp Val
    210                 215                 220

Gly
225
```

<210> SEQ ID NO 2
<211> LENGTH: 281
<212> TYPE: PRT
<213> ORGANISM: Saccharomyces cerevisiae
<220> FEATURE:
<221> NAME/KEY: MISC_FEATURE
<222> LOCATION: (1)..(281)
<223> OTHER INFORMATION: GCN4

<400> SEQUENCE: 2

```
Met Ser Glu Tyr Gln Pro Ser Leu Phe Ala Leu Asn Pro Met Gly Phe
1               5                   10                  15

Ser Pro Leu Asp Gly Ser Lys Ser Thr Asn Glu Asn Val Ser Ala Ser
                20                  25                  30

Thr Ser Thr Ala Lys Pro Met Val Gly Gln Leu Ile Phe Asp Lys Phe
```

```
            35                  40                  45
Ile Lys Thr Glu Glu Asp Pro Ile Ile Lys Gln Asp Thr Pro Ser Asn
 50                  55                  60

Leu Asp Phe Asp Phe Ala Leu Pro Gln Thr Ala Thr Ala Pro Asp Ala
 65                  70                  75                  80

Lys Thr Val Leu Pro Ile Pro Glu Leu Asp Ala Val Val Glu Ser
                     85                  90                  95

Phe Phe Ser Ser Ser Thr Asp Ser Thr Pro Met Phe Glu Tyr Glu Asn
                    100                 105                 110

Leu Glu Asp Asn Ser Lys Glu Trp Thr Ser Leu Phe Asp Asn Asp Ile
                    115                 120                 125

Pro Val Thr Thr Asp Asp Val Ser Leu Ala Asp Lys Ala Ile Glu Ser
                    130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                    165                 170                 175

Arg Lys Val Lys Lys Pro Asn Ser Val Val Lys Lys Ser His His Val
                    180                 185                 190

Gly Lys Asp Asp Glu Ser Arg Leu Asp His Leu Gly Val Val Ala Tyr
                    195                 200                 205

Asn Arg Lys Gln Arg Ser Ile Pro Leu Ser Pro Ile Val Pro Glu Ser
210                 215                 220

Ser Asp Pro Ala Ala Leu Lys Arg Ala Arg Asn Thr Glu Ala Ala Arg
225                 230                 235                 240

Arg Ser Arg Ala Arg Lys Leu Gln Arg Met Lys Gln Leu Glu Asp Lys
                    245                 250                 255

Val Glu Glu Leu Leu Ser Lys Asn Tyr His Leu Glu Asn Glu Val Ala
                    260                 265                 270

Arg Leu Lys Lys Leu Val Gly Glu Arg
                    275                 280

<210> SEQ ID NO 3
<211> LENGTH: 255
<212> TYPE: PRT
<213> ORGANISM: Artificial Sequence
<220> FEATURE:
<223> OTHER INFORMATION: Synthetic construct, CC1

<400> SEQUENCE: 3

Met Arg Ala Lys Gln Leu Glu Asp Lys Val Glu Glu Leu Leu Ser Lys
  1               5                  10                  15

Asn Tyr His Leu Glu Asn Glu Val Ala Arg Leu Lys Lys Leu Val Gly
                 20                  25                  30

Glu Arg Thr Thr Pro Asn Ser Glu Gly Trp His Asp Gly Tyr Tyr Tyr
                 35                  40                  45

Ser Trp Trp Ser Asp Gly Gly Ala Gln Ala Thr Tyr Thr Asn Leu Glu
 50                  55                  60

Gly Gly Thr Tyr Glu Ile Ser Trp Gly Asp Gly Asn Leu Val Gly
 65                  70                  75                  80

Gly Lys Gly Trp Asn Pro Gly Leu Asn Ala Arg Ala Ile His Phe Glu
                 85                  90                  95

Gly Val Tyr Gln Pro Asn Gly Asn Ser Tyr Leu Ala Val Tyr Gly Trp
                100                 105                 110

Thr Arg Asn Pro Leu Val Glu Tyr Tyr Ile Val Glu Asn Phe Gly Thr
```

```
            115                 120                 125

Tyr Asp Pro Ser Ser Gly Ala Thr Asp Leu Gly Thr Val Glu Cys Asp
            130                 135                 140

Gly Ser Ile Tyr Arg Leu Gly Lys Thr Thr Arg Val Asn Ala Pro Ser
145                 150                 155                 160

Ile Asp Gly Thr Gln Thr Phe Asp Gln Tyr Trp Ser Val Arg Gln Asp
                    165                 170                 175

Lys Arg Thr Ser Gly Thr Val His Thr Gly Cys His Phe Asp Ala Trp
                180                 185                 190

Ala Arg Ala Gly Leu Asn Val Asn Gly Asp His Tyr Tyr Gln Ile Val
            195                 200                 205

Ala Thr Glu Gly Tyr Phe Ser Ser Gly Tyr Ala Arg Ile Thr Val Ala
            210                 215                 220

Asp Val Gly Gln Leu Glu Asp Lys Val Glu Leu Leu Ser Lys Asn
225                 230                 235                 240

Tyr His Leu Glu Asn Glu Val Ala Arg Leu Lys Lys Leu Val Gly
                245                 250                 255

<210> SEQ ID NO 4
<211> LENGTH: 255
<212> TYPE: PRT
<213> ORGANISM: Artificial Sequence
<220> FEATURE:
<223> OTHER INFORMATION: Synthetic construct, CC2

<400> SEQUENCE: 4

Met Arg Ala Lys Gln Leu Glu Gly Lys Val Glu Glu Leu Leu Gly Lys
1               5                   10                  15

Asn Tyr His Leu Glu Gly Glu Val Ala Arg Leu Lys Gly Leu Val Gly
                20                  25                  30

Glu Arg Thr Thr Pro Asn Ser Glu Gly Trp His Asp Gly Tyr Tyr Tyr
            35                  40                  45

Ser Trp Trp Ser Asp Gly Gly Ala Gln Ala Thr Tyr Thr Asn Leu Glu
        50                  55                  60

Gly Gly Thr Tyr Glu Ile Ser Trp Gly Asp Gly Gly Asn Leu Val Gly
65              70                  75                  80

Gly Lys Gly Trp Asn Pro Gly Leu Asn Ala Arg Ala Ile His Phe Glu
                85                  90                  95

Gly Val Tyr Gln Pro Asn Gly Asn Ser Tyr Leu Ala Val Tyr Gly Trp
                100                 105                 110

Thr Arg Asn Pro Leu Val Glu Tyr Tyr Ile Val Glu Asn Phe Gly Thr
            115                 120                 125

Tyr Asp Pro Ser Ser Gly Ala Thr Asp Leu Gly Thr Val Glu Cys Asp
            130                 135                 140

Gly Ser Ile Tyr Arg Leu Gly Lys Thr Thr Arg Val Asn Ala Pro Ser
145                 150                 155                 160

Ile Asp Gly Thr Gln Thr Phe Asp Gln Tyr Trp Ser Val Arg Gln Asp
                    165                 170                 175

Lys Arg Thr Ser Gly Thr Val His Thr Gly Cys His Phe Asp Ala Trp
                180                 185                 190

Ala Arg Ala Gly Leu Asn Val Asn Gly Asp His Tyr Tyr Gln Ile Val
            195                 200                 205

Ala Thr Glu Gly Tyr Phe Ser Ser Gly Tyr Ala Arg Ile Thr Val Ala
            210                 215                 220

Asp Val Gly Gln Leu Glu Gly Lys Val Glu Glu Leu Leu Gly Lys Asn
```

```
                225                 230                 235                 240

Tyr His Leu Glu Gly Glu Val Ala Arg Leu Lys Gly Leu Val Gly
            245                 250                 255

<210> SEQ ID NO 5
<211> LENGTH: 255
<212> TYPE: PRT
<213> ORGANISM: Artificial Sequence
<220> FEATURE:
<223> OTHER INFORMATION: Synthetic construct, CC17

<400> SEQUENCE: 5

Met Arg Ala Lys Gln Leu Glu Asp Lys Ile Glu Glu Leu Leu Ser Lys
1               5                   10                  15

Ile Tyr His Leu Glu Asn Glu Ile Ala Arg Leu Lys Lys Leu Ile Gly
            20                  25                  30

Glu Arg Thr Thr Pro Asn Ser Glu Gly Trp His Asp Gly Tyr Tyr Tyr
        35                  40                  45

Ser Trp Trp Ser Asp Gly Gly Ala Gln Ala Thr Tyr Thr Asn Leu Glu
    50                  55                  60

Gly Gly Thr Tyr Glu Ile Ser Trp Gly Asp Gly Gly Asn Leu Val Gly
65                  70                  75                  80

Gly Lys Gly Trp Asn Pro Gly Leu Asn Ala Arg Ala Ile His Phe Glu
                85                  90                  95

Gly Val Tyr Gln Pro Asn Gly Asn Ser Tyr Leu Ala Val Tyr Gly Trp
            100                 105                 110

Thr Arg Asn Pro Leu Val Glu Tyr Tyr Ile Val Glu Asn Phe Gly Thr
        115                 120                 125

Tyr Asp Pro Ser Ser Gly Ala Thr Asp Leu Gly Thr Val Glu Cys Asp
    130                 135                 140

Gly Ser Ile Tyr Arg Leu Gly Lys Thr Thr Arg Val Asn Ala Pro Ser
145                 150                 155                 160

Ile Asp Gly Thr Gln Thr Phe Asp Gln Tyr Trp Ser Val Arg Gln Asp
                165                 170                 175

Lys Arg Thr Ser Gly Thr Val His Thr Gly Cys His Phe Asp Ala Trp
            180                 185                 190

Ala Arg Ala Gly Leu Asn Val Asn Gly Asp His Tyr Tyr Gln Ile Val
        195                 200                 205

Ala Thr Glu Gly Tyr Phe Ser Ser Gly Tyr Ala Arg Ile Thr Val Ala
    210                 215                 220

Asp Val Gly Gln Leu Glu Asp Lys Ile Glu Glu Leu Leu Ser Lys Ile
225                 230                 235                 240

Tyr His Leu Glu Asn Glu Ile Ala Arg Leu Lys Lys Leu Ile Gly
                245                 250                 255

<210> SEQ ID NO 6
<211> LENGTH: 254
<212> TYPE: PRT
<213> ORGANISM: Artificial Sequence
<220> FEATURE:
<223> OTHER INFORMATION: Synthetic construct, CC13

<400> SEQUENCE: 6

Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30
```

Glu Arg Thr Thr Pro Asn Ser Glu Gly Trp His Asp Gly Tyr Tyr Tyr
            35                  40                  45

Ser Trp Trp Ser Asp Gly Gly Ala Gln Ala Thr Tyr Thr Asn Leu Glu
 50                  55                  60

Gly Gly Thr Tyr Glu Ile Ser Trp Gly Asp Gly Gly Asn Leu Val Gly
 65                  70                  75                  80

Gly Lys Gly Trp Asn Pro Gly Leu Asn Ala Arg Ala Ile His Phe Glu
                85                  90                  95

Gly Val Tyr Gln Pro Asn Gly Asn Ser Tyr Leu Ala Val Tyr Gly Trp
                100                 105                 110

Thr Arg Asn Pro Leu Val Glu Tyr Tyr Ile Val Glu Asn Phe Gly Thr
                115                 120                 125

Tyr Asp Pro Ser Ser Gly Ala Thr Asp Leu Gly Thr Val Glu Cys Asp
130                 135                 140

Gly Ser Ile Tyr Arg Leu Gly Lys Thr Thr Arg Val Asn Ala Pro Ser
145                 150                 155                 160

Ile Asp Gly Thr Gln Thr Phe Asp Gln Tyr Trp Ser Val Arg Gln Asp
                165                 170                 175

Lys Arg Thr Ser Gly Thr Val His Thr Gly Cys His Phe Asp Ala Trp
                180                 185                 190

Ala Arg Ala Gly Leu Asn Val Asn Gly Asp His Tyr Tyr Gln Ile Val
                195                 200                 205

Ala Thr Glu Gly Tyr Phe Ser Ser Gly Tyr Ala Arg Ile Thr Val Ala
                210                 215                 220

Asp Gly Gln Leu Glu Asp Lys Val Glu Leu Leu Ser Lys Asn Tyr
225                 230                 235                 240

His Leu Glu Asn Glu Val Ala Arg Leu Lys Lys Leu Val Gly
                245                 250

<210> SEQ ID NO 7
<211> LENGTH: 254
<212> TYPE: PRT
<213> ORGANISM: Artificial Sequence
<220> FEATURE:
<223> OTHER INFORMATION: Synthetic construct, CC14-1

<400> SEQUENCE: 7

Met Arg Ala Lys Gln Leu Glu Asp Lys Val Glu Glu Leu Leu Ser Lys
 1               5                  10                  15

Asn Tyr His Leu Glu Asn Glu Val Ala Arg Leu Lys Lys Leu Val Gly
                20                  25                  30

Glu Thr Thr Pro Asn Ser Glu Gly Trp His Asp Gly Tyr Tyr Tyr Ser
                35                  40                  45

Trp Trp Ser Asp Gly Gly Ala Gln Ala Thr Tyr Thr Asn Leu Glu Gly
 50                  55                  60

Gly Thr Tyr Glu Ile Ser Trp Gly Asp Gly Gly Asn Leu Val Gly Gly
 65                  70                  75                  80

Lys Gly Trp Asn Pro Gly Leu Asn Ala Arg Ala Ile His Phe Glu Gly
                85                  90                  95

Val Tyr Gln Pro Asn Gly Asn Ser Tyr Leu Ala Val Tyr Gly Trp Thr
                100                 105                 110

Arg Asn Pro Leu Val Glu Tyr Tyr Ile Val Glu Asn Phe Gly Thr Tyr
                115                 120                 125

Asp Pro Ser Ser Gly Ala Thr Asp Leu Gly Thr Val Glu Cys Asp Gly
130                 135                 140

```
Ser Ile Tyr Arg Leu Gly Lys Thr Thr Arg Val Asn Ala Pro Ser Ile
145                 150                 155                 160

Asp Gly Thr Gln Thr Phe Asp Gln Tyr Trp Ser Val Arg Gln Asp Lys
                165                 170                 175

Arg Thr Ser Gly Thr Val His Thr Gly Cys His Phe Asp Ala Trp Ala
            180                 185                 190

Arg Ala Gly Leu Asn Val Asn Gly Asp His Tyr Tyr Gln Ile Val Ala
        195                 200                 205

Thr Glu Gly Tyr Phe Ser Ser Gly Tyr Ala Arg Ile Thr Val Ala Asp
    210                 215                 220

Val Gly Gln Leu Glu Asp Lys Val Glu Leu Leu Ser Lys Asn Tyr
225                 230                 235                 240

His Leu Glu Asn Glu Val Ala Arg Leu Lys Lys Leu Val Gly
                245                 250

<210> SEQ ID NO 8
<211> LENGTH: 253
<212> TYPE: PRT
<213> ORGANISM: Artificial Sequence
<220> FEATURE:
<223> OTHER INFORMATION: Synthetic construct, CC14-2

<400> SEQUENCE: 8

Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
                20                  25                  30

Glu Thr Thr Pro Asn Ser Glu Gly Trp His Asp Gly Tyr Tyr Tyr Ser
            35                  40                  45

Trp Trp Ser Asp Gly Gly Ala Gln Ala Thr Tyr Thr Asn Leu Glu Gly
        50                  55                  60

Gly Thr Tyr Glu Ile Ser Trp Gly Asp Gly Gly Asn Leu Val Gly Gly
65                  70                  75                  80

Lys Gly Trp Asn Pro Gly Leu Asn Ala Arg Ala Ile His Phe Glu Gly
                85                  90                  95

Val Tyr Gln Pro Asn Gly Asn Ser Tyr Leu Ala Val Tyr Gly Trp Thr
            100                 105                 110

Arg Asn Pro Leu Val Glu Tyr Tyr Ile Val Glu Asn Phe Gly Thr Tyr
        115                 120                 125

Asp Pro Ser Ser Gly Ala Thr Asp Leu Gly Thr Val Glu Cys Asp Gly
    130                 135                 140

Ser Ile Tyr Arg Leu Gly Lys Thr Thr Arg Val Asn Ala Pro Ser Ile
145                 150                 155                 160

Asp Gly Thr Gln Thr Phe Asp Gln Tyr Trp Ser Val Arg Gln Asp Lys
                165                 170                 175

Arg Thr Ser Gly Thr Val His Thr Gly Cys His Phe Asp Ala Trp Ala
            180                 185                 190

Arg Ala Gly Leu Asn Val Asn Gly Asp His Tyr Tyr Gln Ile Val Ala
        195                 200                 205

Thr Glu Gly Tyr Phe Ser Ser Gly Tyr Ala Arg Ile Thr Val Ala Asp
    210                 215                 220

Gly Gln Leu Glu Asp Lys Val Glu Glu Leu Leu Ser Lys Asn Tyr His
225                 230                 235                 240

Leu Glu Asn Glu Val Ala Arg Leu Lys Lys Leu Val Gly
                245                 250
```

<210> SEQ ID NO 9
<211> LENGTH: 252
<212> TYPE: PRT
<213> ORGANISM: Artificial Sequence
<220> FEATURE:
<223> OTHER INFORMATION: Synthetic construct, CC15

<400> SEQUENCE: 9

```
Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Thr Thr Pro Asn Ser Glu Gly Trp His Asp Gly Tyr Tyr Tyr Ser
        35                  40                  45

Trp Trp Ser Asp Gly Gly Ala Gln Ala Thr Tyr Thr Asn Leu Glu Gly
    50                  55                  60

Gly Thr Tyr Glu Ile Ser Trp Gly Asp Gly Gly Asn Leu Val Gly Gly
65                  70                  75                  80

Lys Gly Trp Asn Pro Gly Leu Asn Ala Arg Ala Ile His Phe Glu Gly
                85                  90                  95

Val Tyr Gln Pro Asn Gly Asn Ser Tyr Leu Ala Val Tyr Gly Trp Thr
            100                 105                 110

Arg Asn Pro Leu Val Glu Tyr Tyr Ile Val Glu Asn Phe Gly Thr Tyr
        115                 120                 125

Asp Pro Ser Ser Gly Ala Thr Asp Leu Gly Thr Val Glu Cys Asp Gly
    130                 135                 140

Ser Ile Tyr Arg Leu Gly Lys Thr Thr Arg Val Asn Ala Pro Ser Ile
145                 150                 155                 160

Asp Gly Thr Gln Thr Phe Asp Gln Tyr Trp Ser Val Arg Gln Asp Lys
                165                 170                 175

Arg Thr Ser Gly Thr Val His Thr Gly Cys His Phe Asp Ala Trp Ala
            180                 185                 190

Arg Ala Gly Leu Asn Val Asn Gly Asp His Tyr Tyr Gln Ile Val Ala
        195                 200                 205

Thr Glu Gly Tyr Phe Ser Ser Gly Tyr Ala Arg Ile Thr Val Ala Gly
    210                 215                 220

Gln Leu Glu Asp Lys Val Glu Glu Leu Leu Ser Lys Asn Tyr His Leu
225                 230                 235                 240

Glu Asn Glu Val Ala Arg Leu Lys Lys Leu Val Gly
                245                 250
```

<210> SEQ ID NO 10
<211> LENGTH: 256
<212> TYPE: PRT
<213> ORGANISM: Artificial Sequence
<220> FEATURE:
<223> OTHER INFORMATION: Synthetic construct, CC22

<400> SEQUENCE: 10

```
Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg Thr Thr Pro Asn Ser Glu Gly Trp His Asp Gly Tyr Tyr Tyr
        35                  40                  45

Ser Trp Trp Ser Asp Gly Gly Ala Gln Ala Thr Tyr Thr Asn Leu Glu
    50                  55                  60
```

-continued

Gly Gly Thr Tyr Glu Ile Ser Trp Gly Asp Gly Asn Leu Val Gly
65                  70                  75                  80

Gly Lys Gly Trp Asn Pro Gly Leu Asn Ala Arg Ala Ile His Phe Glu
            85                  90                  95

Gly Val Tyr Gln Pro Asn Gly Asn Ser Tyr Leu Ala Val Tyr Gly Trp
            100                 105                 110

Thr Arg Asn Pro Leu Val Glu Tyr Tyr Ile Val Glu Asn Phe Gly Thr
            115                 120                 125

Tyr Asp Pro Ser Ser Gly Ala Thr Asp Leu Gly Thr Val Glu Cys Asp
130                 135                 140

Gly Ser Ile Tyr Arg Leu Gly Lys Thr Thr Arg Val Asn Ala Pro Ser
145                 150                 155                 160

Ile Asp Gly Thr Gln Thr Phe Asp Gln Tyr Trp Ser Val Arg Gln Asp
            165                 170                 175

Lys Arg Thr Ser Gly Thr Val His Thr Gly Cys His Phe Asp Ala Trp
            180                 185                 190

Ala Arg Ala Gly Leu Asn Val Asn Gly Asp His Tyr Tyr Gln Ile Val
            195                 200                 205

Ala Thr Glu Gly Tyr Phe Ser Ser Gly Tyr Ala Arg Ile Thr Val Ala
210                 215                 220

Asp Val Gly Ser Gln Leu Glu Asp Lys Val Glu Glu Leu Leu Ser Lys
225                 230                 235                 240

Asn Tyr His Leu Glu Asn Glu Val Ala Arg Leu Lys Lys Leu Val Gly
            245                 250                 255

<210> SEQ ID NO 11
<211> LENGTH: 256
<212> TYPE: PRT
<213> ORGANISM: Artificial Sequence
<220> FEATURE:
<223> OTHER INFORMATION: Synthetic construct, CC23

<400> SEQUENCE: 11

Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg Gln Thr Thr Pro Asn Ser Glu Gly Trp His Asp Gly Tyr Tyr
            35                  40                  45

Tyr Ser Trp Trp Ser Asp Gly Ala Gln Ala Thr Tyr Thr Asn Leu
50                  55                  60

Glu Gly Gly Thr Tyr Glu Ile Ser Trp Gly Asp Gly Asn Leu Val
65                  70                  75                  80

Gly Gly Lys Gly Trp Asn Pro Gly Leu Asn Ala Arg Ala Ile His Phe
            85                  90                  95

Glu Gly Val Tyr Gln Pro Asn Gly Asn Ser Tyr Leu Ala Val Tyr Gly
            100                 105                 110

Trp Thr Arg Asn Pro Leu Val Glu Tyr Tyr Ile Val Glu Asn Phe Gly
            115                 120                 125

Thr Tyr Asp Pro Ser Ser Gly Ala Thr Asp Leu Gly Thr Val Glu Cys
130                 135                 140

Asp Gly Ser Ile Tyr Arg Leu Gly Lys Thr Thr Arg Val Asn Ala Pro
145                 150                 155                 160

Ser Ile Asp Gly Thr Gln Thr Phe Asp Gln Tyr Trp Ser Val Arg Gln
            165                 170                 175

Asp Lys Arg Thr Ser Gly Thr Val His Thr Gly Cys His Phe Asp Ala
            180                 185                 190

Trp Ala Arg Ala Gly Leu Asn Val Asn Gly Asp His Tyr Tyr Gln Ile
            195                 200                 205

Val Ala Thr Glu Gly Tyr Phe Ser Ser Gly Tyr Ala Arg Ile Thr Val
            210                 215                 220

Ala Asp Val Gly Gln Leu Glu Asp Lys Val Glu Glu Leu Leu Ser Lys
225                 230                 235                 240

Asn Tyr His Leu Glu Asn Glu Val Ala Arg Leu Lys Lys Leu Val Gly
                245                 250                 255

<210> SEQ ID NO 12
<211> LENGTH: 257
<212> TYPE: PRT
<213> ORGANISM: Artificial Sequence
<220> FEATURE:
<223> OTHER INFORMATION: Synthetic construct, CC24

<400> SEQUENCE: 12

Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg Gln Thr Thr Pro Asn Ser Glu Gly Trp His Asp Gly Tyr Tyr
        35                  40                  45

Tyr Ser Trp Trp Ser Asp Gly Ala Gln Ala Thr Tyr Thr Asn Leu
    50                  55                  60

Glu Gly Gly Thr Tyr Glu Ile Ser Trp Gly Asp Gly Gly Asn Leu Val
65                  70                  75                  80

Gly Gly Lys Gly Trp Asn Pro Gly Leu Asn Ala Arg Ala Ile His Phe
                85                  90                  95

Glu Gly Val Tyr Gln Pro Asn Gly Asn Ser Tyr Leu Ala Val Tyr Gly
            100                 105                 110

Trp Thr Arg Asn Pro Leu Val Glu Tyr Tyr Ile Val Glu Asn Phe Gly
        115                 120                 125

Thr Tyr Asp Pro Ser Ser Gly Ala Thr Asp Leu Gly Thr Val Glu Cys
130                 135                 140

Asp Gly Ser Ile Tyr Arg Leu Gly Lys Thr Thr Arg Val Asn Ala Pro
145                 150                 155                 160

Ser Ile Asp Gly Thr Gln Thr Phe Asp Gln Tyr Trp Ser Val Arg Gln
            165                 170                 175

Asp Lys Arg Thr Ser Gly Thr Val His Thr Gly Cys His Phe Asp Ala
        180                 185                 190

Trp Ala Arg Ala Gly Leu Asn Val Asn Gly Asp His Tyr Tyr Gln Ile
    195                 200                 205

Val Ala Thr Glu Gly Tyr Phe Ser Ser Gly Tyr Ala Arg Ile Thr Val
        210                 215                 220

Ala Asp Val Gly Ser Gln Leu Glu Asp Lys Val Glu Glu Leu Leu Ser
225                 230                 235                 240

Lys Asn Tyr His Leu Glu Asn Glu Val Ala Arg Leu Lys Lys Leu Val
                245                 250                 255

Gly

<210> SEQ ID NO 13
<211> LENGTH: 255

```
<212> TYPE: PRT
<213> ORGANISM: Artificial Sequence
<220> FEATURE:
<223> OTHER INFORMATION: Synthetic construct, CC30

<400> SEQUENCE: 13

Met Arg Ala Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Thr Arg Thr Thr Pro Asn Ser Glu Gly Trp His Asp Gly Tyr Tyr Tyr
        35                  40                  45

Ser Trp Trp Ser Asp Gly Gly Ala Gln Ala Thr Tyr Thr Asn Leu Glu
50                  55                  60

Gly Gly Thr Tyr Glu Ile Ser Trp Gly Asp Gly Asn Leu Val Gly
65                  70                  75                  80

Gly Lys Gly Trp Asn Pro Gly Leu Asn Ala Arg Ala Ile His Phe Glu
            85                  90                  95

Gly Val Tyr Gln Pro Asn Gly Asn Ser Tyr Leu Ala Val Tyr Gly Trp
            100                 105                 110

Thr Arg Asn Pro Leu Val Glu Tyr Tyr Ile Val Glu Asn Phe Gly Thr
        115                 120                 125

Tyr Asp Pro Ser Ser Gly Ala Thr Asp Leu Gly Thr Val Glu Cys Asp
130                 135                 140

Gly Ser Ile Tyr Arg Leu Gly Lys Thr Thr Arg Val Asn Ala Pro Ser
145                 150                 155                 160

Ile Asp Gly Thr Gln Thr Phe Asp Gln Tyr Trp Ser Val Arg Gln Asp
                165                 170                 175

Lys Arg Thr Ser Gly Thr Val His Thr Gly Cys His Phe Asp Ala Trp
            180                 185                 190

Ala Arg Ala Gly Leu Asn Val Asn Gly Asp His Tyr Tyr Gln Ile Val
        195                 200                 205

Ala Thr Glu Gly Tyr Phe Ser Ser Gly Tyr Ala Arg Ile Thr Val Ala
210                 215                 220

Asp Val Gly Gln Leu Glu Asp Lys Val Glu Glu Leu Leu Ser Lys Asn
225                 230                 235                 240

Tyr His Leu Glu Asn Glu Val Ala Arg Leu Lys Lys Leu Val Gly
            245                 250                 255

<210> SEQ ID NO 14
<211> LENGTH: 382
<212> TYPE: PRT
<213> ORGANISM: Fusarium oxysporum
<220> FEATURE:
<221> NAME/KEY: MISC_FEATURE
<222> LOCATION: (1)..(382)
<223> OTHER INFORMATION: BD25243

<400> SEQUENCE: 14

Met Lys Ser Leu Phe Ala Leu Ser Leu Phe Ala Gly Leu Ser Val Ala
1               5                   10                  15

Gln Asn Ala Ala Trp Ala Gln Cys Gly Gly Asn Gly Trp Thr Gly Ser
            20                  25                  30

Lys Thr Cys Val Ser Gly Tyr Lys Cys Thr Val Val Asn Glu Trp Tyr
        35                  40                  45

Ser Gln Cys Ile Pro Gly Thr Ala Glu Glu Pro Thr Thr Thr Leu Lys
50                  55                  60
```

```
Thr Thr Thr Gly Gly Gly Ser Thr Pro Thr Gly Pro Gly Asn Gly
 65                  70                  75                  80

Lys Phe Leu Trp Val Gly Thr Asn Glu Ala Gly Gly Glu Phe Gly Glu
                 85                  90                  95

Gly Ser Leu Pro Gly Thr Trp Gly Lys His Phe Ile Phe Pro Asp Pro
            100                 105                 110

Ala Ala Val Asp Thr Leu Ile Ser Gln Gly Tyr Asn Ala Phe Arg Val
            115                 120                 125

Gln Leu Arg Met Glu Arg Thr Asn Pro Ser Ser Met Thr Gly Pro Phe
        130                 135                 140

Asp Thr Ala Tyr Leu Lys Asn Leu Thr Thr Ile Val Asp His Ile Thr
145                 150                 155                 160

Gly Lys Gly Ala Asn Val Ile Leu Asp Pro His Asn Tyr Gly Arg Tyr
                165                 170                 175

Phe Asp Lys Ile Ile Thr Ser Thr Ser Asp Phe Gln Thr Trp Trp Lys
            180                 185                 190

Asn Phe Ala Thr Gln Phe Lys Ser Asn Ser Lys Val Ile Phe Asp Thr
        195                 200                 205

Asn Asn Glu Tyr Asn Thr Met Asp Gln Thr Leu Val Leu Asn Leu Asn
210                 215                 220

Gln Ala Ala Ile Asn Gly Ile Arg Ala Ala Gly Ala Thr Gln Thr Ile
225                 230                 235                 240

Phe Val Glu Gly Asn Gln Trp Ser Gly Ala Trp Ser Trp Pro Asp Val
                245                 250                 255

Asn Asp Asn Met Lys Ala Leu Thr Asp Pro Leu Asp Lys Ile Val Tyr
            260                 265                 270

Glu Met His Gln Tyr Leu Asp Ser Asp Ser Ser Gly Thr Ser Pro Asn
        275                 280                 285

Cys Val Ser Thr Thr Ile Gly Val Glu Arg Val Lys Ala Ala Thr Glu
290                 295                 300

Trp Leu Arg Lys Asn Lys Lys Ile Gly Met Ile Gly Glu Leu Ala Gly
305                 310                 315                 320

Gly Pro Asn Asp Thr Cys Lys Thr Ala Val Lys Asn Met Leu Asp Tyr
                325                 330                 335

Leu Lys Glu Asn Ser Asp Val Trp Lys Gly Val Thr Trp Trp Ala Ala
            340                 345                 350

Gly Pro Trp Trp Ala Asp Tyr Met Phe Ser Phe Glu Pro Pro Ser Gly
        355                 360                 365

Thr Gly Tyr Gln Tyr Tyr Asn Ser Leu Leu Lys Thr Tyr Ile
370                 375                 380

<210> SEQ ID NO 15
<211> LENGTH: 428
<212> TYPE: PRT
<213> ORGANISM: Artificial Sequence
<220> FEATURE:
<223> OTHER INFORMATION: Synthetic construct, BD25CC2

<400> SEQUENCE: 15

Met Ala Gln Asn Ala Ala Trp Ala Gln Cys Gly Gly Asn Gly Trp Thr
  1               5                  10                  15

Gly Ser Lys Thr Cys Val Ser Gly Tyr Lys Cys Thr Val Val Asn Glu
                 20                  25                  30

Trp Tyr Ser Gln Cys Ile Pro Gly Thr Ala Glu Glu Pro Thr Thr Thr
             35                  40                  45
```

Leu Lys Thr Thr Thr Gly Gly Gly Ser Thr Pro Thr Gly Arg Ala Lys
 50                  55                  60

Gln Leu Glu Asp Lys Val Glu Glu Leu Leu Ser Lys Asn Tyr His Leu
 65                  70                  75                  80

Glu Asn Glu Val Ala Arg Leu Lys Lys Leu Val Gly Pro Gly Asn Gly
                 85                  90                  95

Lys Phe Leu Trp Val Gly Thr Asn Glu Ala Gly Gly Glu Phe Gly Glu
            100                 105                 110

Gly Ser Leu Pro Gly Thr Trp Gly Lys His Phe Ile Phe Pro Asp Pro
        115                 120                 125

Ala Ala Val Asp Thr Leu Ile Ser Gln Gly Tyr Asn Ala Phe Arg Val
130                 135                 140

Gln Leu Arg Met Glu Arg Thr Asn Pro Ser Ser Met Thr Gly Pro Phe
145                 150                 155                 160

Asp Thr Ala Tyr Leu Lys Asn Leu Thr Thr Ile Val Asp His Ile Thr
                165                 170                 175

Gly Lys Gly Ala Asn Val Ile Leu Asp Pro His Asn Tyr Gly Arg Tyr
            180                 185                 190

Phe Asp Lys Ile Ile Thr Ser Thr Ser Asp Phe Gln Thr Trp Trp Lys
        195                 200                 205

Asn Phe Ala Thr Gln Phe Lys Ser Asn Ser Lys Val Ile Phe Asp Thr
210                 215                 220

Asn Asn Glu Tyr Asn Thr Met Asp Gln Thr Leu Val Leu Asn Leu Asn
225                 230                 235                 240

Gln Ala Ala Ile Asn Gly Ile Arg Ala Ala Gly Ala Thr Gln Thr Ile
                245                 250                 255

Phe Val Glu Gly Asn Gln Trp Ser Gly Ala Trp Ser Trp Pro Asp Val
            260                 265                 270

Asn Asp Asn Met Lys Ala Leu Thr Asp Pro Leu Asp Lys Ile Val Tyr
        275                 280                 285

Glu Met His Gln Tyr Leu Asp Ser Asp Ser Gly Thr Ser Pro Asn
290                 295                 300

Cys Val Ser Thr Thr Ile Gly Val Glu Arg Val Lys Ala Ala Thr Glu
305                 310                 315                 320

Trp Leu Arg Lys Asn Lys Lys Ile Gly Met Ile Gly Glu Leu Ala Gly
                325                 330                 335

Gly Pro Asn Asp Thr Cys Lys Thr Ala Val Lys Asn Met Leu Asp Tyr
            340                 345                 350

Leu Lys Glu Asn Ser Asp Val Trp Lys Gly Val Thr Trp Trp Ala Ala
        355                 360                 365

Gly Pro Trp Trp Ala Asp Tyr Met Phe Ser Phe Glu Pro Pro Ser Gly
370                 375                 380

Thr Gly Tyr Gln Tyr Tyr Asn Ser Leu Leu Lys Thr Tyr Ile Gly Ser
385                 390                 395                 400

Gln Leu Glu Asp Lys Val Glu Glu Leu Leu Ser Lys Asn Tyr His Leu
                405                 410                 415

Glu Asn Glu Val Ala Arg Leu Lys Lys Leu Val Gly
            420                 425

<210> SEQ ID NO 16
<211> LENGTH: 624
<212> TYPE: DNA
<213> ORGANISM: Artificial Sequence
<220> FEATURE:
<223> OTHER INFORMATION: Synthetic construct, O43T, nucleic acid

<400> SEQUENCE: 16

```
atgttcccag ctggaaacgc aacggaattg gagaaaagac aaaccacccc taactctgag      60
ggctggcatg acggatacta ctactcttgg tggagcgatg gtggtgcaca ggccacctat     120
acaaacctcg aaggcggcac ttatgagatt tcatggggtg acggtggcaa ccttgtcggc     180
ggaaaggggt ggaaccccgg acttaacgcc agggcaatcc acttcgaagg ggtgtaccag     240
cccaatggca actcatacct ggccgtctac gggtggacgc gcaatccgct ggttgagtac     300
tatatcgtgg agaatttcgg aacttatgac cctagctccg gtgccacgga cctcgggaca     360
gtcgagtgtg acgaagcat  ctacaggctg gtaaaacta  cccgcgttaa tgctccatcg     420
atcgacggca cgcaaacatt tgatcaatac tggtccgtgc ggcaggataa gaggacaagc     480
ggcacagttc atacggggttg ccactttgat gcctgggcaa gagcggggct caatgtgaat    540
ggggaccact actatcagat tgtggcgacc gagggctatt tctccagtgg ctatgcgcgt    600
ataaccgtgg cagatgttgg ctaa                                            624
```

<210> SEQ ID NO 17
<211> LENGTH: 846
<212> TYPE: DNA
<213> ORGANISM: Saccharomyces cerevisiae
<220> FEATURE:
<221> NAME/KEY: misc_feature
<222> LOCATION: (1)..(846)
<223> OTHER INFORMATION: GCN4, nucleic acid

<400> SEQUENCE: 17

```
atgtccgaat atcagccaag tttatttgct ttaaatccaa tgggtttctc accattggat      60
ggttctaaat caaccaacga aaatgtatct gcttccactt ctactgccaa accaatggtt    120
ggccaattga tttttgataa attcatcaag actgaagagg atccaattat caaacaggat    180
accccttcga accttgattt tgattttgct cttccacaaa cggcaactgc acctgatgcc    240
aagaccgttt tgccaattcc ggagctagat gacgctgtag tggaatcttt cttttcgtca    300
agcactgatt caactccaat gtttgagtat gaaaacctag aagacaactc taaagaatgg    360
acatccttgt ttgacaatga cattccagtt accactgacg atgtttcatt ggctgataag    420
gcaattgaat ccactgaaga gtttctctg  gtaccatcca atctggaagt ctcgacaact    480
tcattcttac ccactcctgt tctagaagat gctaaactga ctcaaacaag aaaggttaag    540
aaaccaaatt cagtcgttaa gaagtcacat catgttggaa aggatgacga atcgagactg    600
gatcatctag gtgttgttgc ttacaaccgc aaacagcgtt cgattccact ttctccaatt    660
gtgcccgaat ccagtgatcc tgctgctcta aaacgtgcta gaaacactga agccgccagg    720
cgttctcgtg cgagaaagtt gcaaagaatg aaacaacttg aagacaaggt tgaagaattg    780
ctttcgaaaa attatcactt ggaaaatgag gttgccagat taaagaaatt agttggcgaa    840
cgctga                                                                846
```

<210> SEQ ID NO 18
<211> LENGTH: 768
<212> TYPE: DNA
<213> ORGANISM: Artificial Sequence
<220> FEATURE:
<223> OTHER INFORMATION: Synthetic construct, CC1, nucleic acid

<400> SEQUENCE: 18

```
atgagggcca agcagctgga ggacaaggtc gaggagctgc tgagcaagaa ctaccaccctg     60
```

| gagaacgagg tcgcccgcct gaagaagctg gtgggcgagc gcaccacccc taactctgag | 120 |
| ggctggcatg acggatacta ctactcttgg tggagcgatg gtggtgcaca ggccacctat | 180 |
| acaaacctcg aaggcggcac ttatgagatt tcatggggtg acggtggcaa ccttgtcggc | 240 |
| ggaaaggggt ggaaccccgg acttaacgcc agggcaatcc acttcgaagg ggtgtaccag | 300 |
| cccaatggca actcatacct ggccgtctac gggtggacgc gcaatccgct ggttgagtac | 360 |
| tatatcgtgg agaatttcgg aacttatgac cctagctccg gtgccacgga cctcgggaca | 420 |
| gtcgagtgtg acggaagcat ctacaggctg gtaaaacta cccgcgttaa tgctccatcg | 480 |
| atcgacggca cgcaaacatt tgatcaatac tggtccgtgc ggcaggataa gaggacaagc | 540 |
| ggcacagttc atacgggttg ccactttgat gcctgggcaa gagcggggct caatgtgaat | 600 |
| ggggaccact actatcagat tgtggcgacc gagggctatt tctccagtgg ctatgcgcgt | 660 |
| ataaccgtgg cagatgttgg ccaattggaa gataaagtgg aagagctcct gtccaaaaat | 720 |
| tatcatctgg aaaatgaggt ggcccgcttg aagaaactcg tgggataa | 768 |

<210> SEQ ID NO 19
<211> LENGTH: 768
<212> TYPE: DNA
<213> ORGANISM: Artificial Sequence
<220> FEATURE:
<223> OTHER INFORMATION: Synthetic construct, CC2, nucleic acid

<400> SEQUENCE: 19

| atgagggcga agcagctgga gggcaaggtc gaggagctgc tgggcaagaa ctaccacctg | 60 |
| gagggcgagg tggcgaggct gaagggcctg gtgggcgagc gcaccacccc taactctgag | 120 |
| ggctggcatg acggatacta ctactcttgg tggagcgatg gtggtgcaca ggccacctat | 180 |
| acaaacctcg aaggcggcac ttatgagatt tcatggggtg acggtggcaa ccttgtcggc | 240 |
| ggaaaggggt ggaaccccgg acttaacgcc agggcaatcc acttcgaagg ggtgtaccag | 300 |
| cccaatggca actcatacct ggccgtctac gggtggacgc gcaatccgct ggttgagtac | 360 |
| tatatcgtgg agaatttcgg aacttatgac cctagctccg gtgccacgga cctcgggaca | 420 |
| gtcgagtgtg acggaagcat ctacaggctg gtaaaacta cccgcgttaa tgctccatcg | 480 |
| atcgacggca cgcaaacatt tgatcaatac tggtccgtgc ggcaggataa gaggacaagc | 540 |
| ggcacagttc atacgggttg ccactttgat gcctgggcaa gagcggggct caatgtgaat | 600 |
| ggggaccact actatcagat tgtggcgacc gagggctatt tctccagtgg ctatgcgcgt | 660 |
| ataaccgtgg cagatgttgg ccagctggag ggcaaggtcg aggagctgct gggcaagaac | 720 |
| taccacctgg agggcgaggt ggcgaggctg aagggcctgg tcggctaa | 768 |

<210> SEQ ID NO 20
<211> LENGTH: 782
<212> TYPE: DNA
<213> ORGANISM: Artificial Sequence
<220> FEATURE:
<223> OTHER INFORMATION: Synthetic construct, CC17, nucleic acid

<400> SEQUENCE: 20

| atgagggcca agcagctgga ggacaagatt gaggagctgc tgagcaagat ctaccacctg | 60 |
| gagaacgaga tagcccgcct gaagaagctg attggcgagc gcaccacccc taactctgag | 120 |
| ggctggcatg acggatacta ctactcttgg tggagcgatg gtggtgcaca ggccacctat | 180 |
| acaaacctcg aaggcggcac ttatgagatt tcatggggtg acggtggcaa ccttgtcggc | 240 |
| ggaaaggggt ggaaccccgg acttaacgcc agggcaatcc acttcgaagg ggtgtaccag | 300 |

```
cccaatggca actcatacct ggccgtctac gggtggacgc gcaatccgct ggttgagtac      360
tatatcgtgg agaatttcgg aacttatgac cctagctccg gtgccacgga cctcgggaca      420
gtcgagtgtg acggaagcat ctacaggctg gtaaaacta cccgcgttaa tgctccatcg       480
atcgacggca cgcaaacatt tgatcaatac tggtccgtgc ggcaggataa gaggacaagc      540
ggcacagttc atacgggttg ccactttgat gcctgggcaa gagcggggct caatgtgaat      600
ggggaccact actatcagat tgtggcgacc gagggctatt tctccagtgg ctatgcgcgt      660
ataaccgtgg cagatgttgg ccagctggag gacaagattg aggagctgct gagcaagatc      720
taccacctgg agaacgagat agcgaggctg aagaagctga ttggcgagcg caccacccct      780
aa                                                                     782
```

```
<210> SEQ ID NO 21
<211> LENGTH: 765
<212> TYPE: DNA
<213> ORGANISM: Artificial Sequence
<220> FEATURE:
<223> OTHER INFORMATION: Synthetic construct, CC13, nucleic acid

<400> SEQUENCE: 21
atgagggcca agcagctgga ggacaaggtc gaggagctgc tgagcaagaa ctaccacctg       60
gagaacgagg tcgcccgcct gaagaagctg gtgggcgagc gcaccacccc taactctgag      120
ggctggcatg acggatacta ctactcttgg tggagcgatg gtggtgcaca ggccacctat      180
acaaacctcg aaggcggcac ttatgagatt tcatggggtg acggtggcaa ccttgtcggc      240
ggaaaggggt ggaaccccgg acttaacgcc agggcaatcc acttcgaagg ggtgtaccag      300
cccaatggca actcatacct ggccgtctac gggtggacgc gcaatccgct ggttgagtac      360
tatatcgtgg agaatttcgg aacttatgac cctagctccg gtgccacgga cctcgggaca      420
gtcgagtgtg acggaagcat ctacaggctg gtaaaacta cccgcgttaa tgctccatcg       480
atcgacggca cgcaaacatt tgatcaatac tggtccgtgc ggcaggataa gaggacaagc      540
ggcacagttc atacgggttg ccactttgat gcctgggcaa gagcggggct caatgtgaat      600
ggggaccact actatcagat tgtggcgacc gagggctatt tctccagtgg ctatgcgcgt      660
ataaccgtgg cagatggcca gctggaggac aaggtcgagg agctgctgag caagaactac      720
cacctggaga acgaggtcgc gaggctgaag aagctggtcg gctaa                      765
```

```
<210> SEQ ID NO 22
<211> LENGTH: 765
<212> TYPE: DNA
<213> ORGANISM: Artificial Sequence
<220> FEATURE:
<223> OTHER INFORMATION: Synthetic construct, CC14-1, nucleic acid

<400> SEQUENCE: 22
atgagggcca agcagctgga ggacaaggtc gaggagctgc tgagcaagaa ctaccacctg       60
gagaacgagg tcgcccgcct gaagaagctg gtgggcgaga ccacccctaa ctctgagggc      120
tggcatgacg gatactacta ctcttggtgg agcgatggtg gtgcacaggc cacctataca      180
aacctcgaag gcggcactta tgagatttca tggggtgacg gtggcaacct tgtcggcgga     240
aaggggtgga accccggact taacgccagg gcaatccact tcgaagggt gtaccagccc       300 aatggcaact catacctggc cgtctacggg tggacgcgca atccgctggt tgagtactat      360
atcgtggaga atttcggaac ttatgaccct agctccggtg ccacggacct cgggacagtc      420
```

```
gagtgtgacg gaagcatcta caggctgggt aaaactaccc gcgttaatgc tccatcgatc    480
gacggcacgc aaacatttga tcaatactgg tccgtgcggc aggataagag acaagcggc     540 acagttcata cgggttgcca cttttgatgcc tgggcaagag cggggctcaa tgtgaatggg   600
gaccactact atcagattgt ggcgaccgag ggctatttct ccagtggcta tgcgcgtata    660
accgtggcag atgttggcca gctggaggac aaggtcgagg agctgctgag caagaactac    720
cacctggaga acgaggtcgc gaggctgaag aagctggtcg gctaa                    765

<210> SEQ ID NO 23
<211> LENGTH: 762
<212> TYPE: DNA
<213> ORGANISM: Artificial Sequence
<220> FEATURE:
<223> OTHER INFORMATION: Synthetic construct, CC14-2, nucleic acid

<400> SEQUENCE: 23
atgagggcca agcagctgga ggacaaggtc gaggagctgc tgagcaagaa ctaccacctg     60
gagaacgagg tcgcccgcct gaagaagctg gtgggcgaga ccaccccctaa ctctgagggc   120 tggcatgacg gatactacta ctcttggtgg agcgatggtg gtgcacaggc cacctataca    180
aacctcgaag gcggcactta tgagatttca tggggtgacg gtggcaacct tgtcggcgga    240
aaggggtgga accccggact taacgccagg gcaatccact cgaagggggt gtaccagccc    300
aatggcaact catacctggc cgtctacggg tggacgcgca atccgctggt tgagtactat    360
atcgtggaga atttcggaac ttatgacccct agctccggtg ccacggacct cgggacagtc    420
gagtgtgacg gaagcatcta caggctgggt aaaactaccc gcgttaatgc tccatcgatc    480
gacggcacgc aaacatttga tcaatactgg tccgtgcggc aggataagag acaagcggc     540 acagttcata cgggttgcca cttttgatgcc tgggcaagag cggggctcaa tgtgaatggg   600
gaccactact atcagattgt ggcgaccgag ggctatttct ccagtggcta tgcgcgtata    660
accgtggcag atggccagct ggaggacaag gtcgaggagc tgctgagcaa gaactaccac    720
ctggagaacg aggtcgcgag gctgaagaag ctggtcggct aa                       762

<210> SEQ ID NO 24
<211> LENGTH: 759
<212> TYPE: DNA
<213> ORGANISM: Artificial Sequence
<220> FEATURE:
<223> OTHER INFORMATION: Synthetic construct, CC15, nucleic acid

<400> SEQUENCE: 24
atgagggcca agcagctgga ggacaaggtc gaggagctgc tgagcaagaa ctaccacctg     60
gagaacgagg tcgcccgcct gaagaagctg gtgggcgaga ccaccccctaa ctctgagggc   120 tggcatgacg gatactacta ctcttggtgg agcgatggtg gtgcacaggc cacctataca    180
aacctcgaag gcggcactta tgagatttca tggggtgacg gtggcaacct tgtcggcgga    240
aaggggtgga accccggact taacgccagg gcaatccact cgaagggggt gtaccagccc    300
aatggcaact catacctggc cgtctacggg tggacgcgca atccgctggt tgagtactat    360
atcgtggaga atttcggaac ttatgacccct agctccggtg ccacggacct cgggacagtc    420
gagtgtgacg gaagcatcta caggctgggt aaaactaccc gcgttaatgc tccatcgatc    480
gacggcacgc aaacatttga tcaatactgg tccgtgcggc aggataagag acaagcggc     540 acagttcata cgggttgcca cttttgatgcc tgggcaagag cggggctcaa tgtgaatggg   600
gaccactact atcagattgt ggcgaccgag ggctatttct ccagtggcta tgcgcgtata    660
```

```
accgtggcag gccagctgga ggacaaggtc gaggagctgc tgagcaagaa ctaccacctg      720
gagaacgagg tcgcgaggct gaagaagctg gtcggctaa                            759
```

<210> SEQ ID NO 25
<211> LENGTH: 771
<212> TYPE: DNA
<213> ORGANISM: Artificial Sequence
<220> FEATURE:
<223> OTHER INFORMATION: Synthetic construct, CC22, nucleic acid

<400> SEQUENCE: 25

```
atgagggcca agcagctgga ggacaaggtc gaggagctgc tgagcaagaa ctaccacctg       60
gagaacgagg tcgcccgcct gaagaagctg gtgggcgagc gcaccacccc taactctgag     120
ggctggcatg acggatacta ctactcttgg tggagcgatg gtggtgcaca ggccacctat     180
acaaacctcg aaggcggcac ttatgagatt catggggtg acggtggcaa ccttgtcggc      240
ggaaaggggt ggaaccccgg acttaacgcc agggcaatcc acttcgaagg ggtgtaccag     300
cccaatggca actcatacct ggccgtctac gggtggacgc gcaatccgct ggttgagtac     360
tatatcgtgg agaatttcgg aacttatgac cctagctccg gtgccacgga cctcgggaca     420
gtcgagtgtg acggaagcat ctacaggctg gtaaaacta cccgcgttaa tgctccatcg      480
atcgacggca cgcaaacatt tgatcaatac tggtccgtgc ggcaggataa gaggacaagc     540
ggcacagttc atacgggttg ccactttgat gcctgggcaa gagcggggct caatgtgaat     600
ggggaccact actatcagat tgtggcgacc gagggctatt tctccagtgg ctatgcgcgt     660
ataaccgtgg cagatgttgg ctcccagctg gaggacaagg tcgaggagct gctgagcaag     720
aactaccacc tggagaacga ggtcgcgagg ctgaagaagc tggtcggcta a               771
```

<210> SEQ ID NO 26
<211> LENGTH: 771
<212> TYPE: DNA
<213> ORGANISM: Artificial Sequence
<220> FEATURE:
<223> OTHER INFORMATION: Synthetic construct, CC23, nucleic acid

<400> SEQUENCE: 26

```
atgagggcca agcagctgga ggacaaggtc gaggagctgc tgagcaagaa ctaccacctg       60
gagaacgagg tcgcccgcct gaagaagctg gtgggcgagc gccagaccac ccctaactct     120
gagggctggc atgacggata ctactactct tggtggagcg atggtggtgc acaggccacc     180
tatacaaacc tcgaaggcgg cacttatgag atttcatggg gtgacggtgg caaccttgtc     240
ggcggaaagg ggtggaaccc cggacttaac gccagggcaa tccacttcga aggggtgtac     300
cagcccaatg gcaactcata cctggccgtc tacgggtgga cgcgcaatcc gctggttgag     360
tactatatcg tggagaattt cggaacttat gaccctagct ccggtgccac ggacctcggg     420
acagtcgagt gtgacggaag catctacagg ctgggtaaaa ctacccgcgt taatgctcca     480
tcgatcgacg gcacgcaaac atttgatcaa tactggtccg tgcggcagga taagaggaca     540
agcggcacag ttcatacggg ttgccacttt gatgcctggg caagagcggg gctcaatgtg     600
aatggggacc actactatca gattgtggcg accgagggct atttctccag tggctatgcg     660
cgtataaccg tggcagatgt tggccagctg gaggacaagg tcgaggagct gctgagcaag     720
aactaccacc tggagaacga ggtcgcgagg ctgaagaagc tggtcggcta a               771
```

<210> SEQ ID NO 27

```
<211> LENGTH: 774
<212> TYPE: DNA
<213> ORGANISM: Artificial Sequence
<220> FEATURE:
<223> OTHER INFORMATION: Synthetic construct, CC24, nucleic acid

<400> SEQUENCE: 27
atgagggcca agcagctgga ggacaaggtc gaggagctgc tgagcaagaa ctaccacctg      60
gagaacgagg tcgcccgcct gaagaagctg gtgggcgagc gccagaccac ccctaactct     120
gagggctggc atgacggata ctactactct tggtggagcg atggtggtgc acaggccacc     180
tatacaaacc tcgaaggcgg cacttatgag atttcatggg gtgacggtgg caaccttgtc     240
ggcggaaagg ggtggaaccc cggacttaac gccagggcaa tccacttcga aggggtgtac     300
cagcccaatg caactcata cctggccgtc tacgggtgga cgcgcaatcc gctggttgag      360
tactatatcg tggagaattt cggaacttat gaccctagct ccggtgccac ggacctcggg     420
acagtcgagt gtgacggaag catctacagg ctgggtaaaa ctacccgcgt taatgctcca     480
tcgatcgacg gcacgcaaac atttgatcaa tactggtccg tgcggcagga taagaggaca     540
agcggcacag ttcatacggg ttgccacttt gatgcctggg caagagcggg gctcaatgtg     600 aatgggacc actactatca gattgtggcg accgagggct atttctccag tggctatgcg      660
cgtataaccg tggcagatgt tggctcccag ctggaggaca aggtcgagga gctgctgagc     720
aagaactacc acctggagaa cgaggtcgcg aggctgaaga agctggtcgg ctaa            774

<210> SEQ ID NO 28
<211> LENGTH: 768
<212> TYPE: DNA
<213> ORGANISM: Artificial Sequence
<220> FEATURE:
<223> OTHER INFORMATION: Synthetic construct, CC30, nucleic acid

<400> SEQUENCE: 28
atgagggcca agcagctgga ggacaaggtc gaggagctgc tgagcaagaa ctaccacctg      60
gagaacgagg tcgcccgcct gaagaagctg gtgggcaccc gcaccacccc taactctgag     120
ggctggcatg acggatacta ctactcttgg tggagcgatg gtggtgcaca ggccacctat     180
acaaacctcg aaggcggcac ttatgagatt tcatggggtg acggtggcaa ccttgtcggc     240
ggaaaggggt ggaaccccgg acttaacgcc agggcaatcc acttcgaagg ggtgtaccag     300
cccaatggca actcatacct ggccgtctac gggtggacgc gcaatccgct ggttgagtac     360
tatatcgtgg agaatttcgg aacttatgac cctagctccg gtgccacgga cctcgggaca     420
gtcgagtgtg acggaagcat ctacaggctg gtaaaacta cccgcgttaa tgctccatcg      480
atcgacggca cgcaaacatt tgatcaatac tggtccgtgc ggcaggataa gaggacaagc     540
ggcacagttc atacgggttg ccactttgat gcctgggcaa gagcggggct caatgtgaat     600
ggggaccact actatcagat tgtggcgacc gagggctatt tctccagtgg ctatgcgcgt     660
ataaccgtgg cagatgttgg ccagctggag gacaaggtcg aggagctgct gagcaagaac     720
taccacctgg agaacgaggt cgcgaggctg aagaagctgg tcggctaa                   768

<210> SEQ ID NO 29
<211> LENGTH: 1104
<212> TYPE: DNA
<213> ORGANISM: Artificial Sequence
<220> FEATURE:
<223> OTHER INFORMATION: Synthetic construct, BD25243, nucleic acid

<400> SEQUENCE: 29
```

```
atggcccaga acgccgcctg ggctcaatgc ggcggcaacg gctggaccgg cagcaagacc      60
tgcgtgtccg gctacaagtg caccgtggtg aacgagtggt actcccagtg catcccgggc     120
accgccgagg aacctaccac caccctcaag accaccaccg gcggcggcag cacccccaacc   180
ggcacccag gcaacggcaa gttcctgtgg gtgggcacga acgaggctgg cggcgagttc      240
ggcgagggca gcctgccagg cacctggggc aagcacttca tcttcccgga cccagccgcc     300
gtggacaccc tgatcagcca gggctacaac gccttccgcg tccagctgcg catggagcgc     360
accaacccga gcagcatgac cggccccttc gacaccgcct acctgaagaa cctgaccacc     420
atcgtggacc acatcaccgg caagggcgcc aacgtgatcc tggacccgca caactacggc     480
cgctacttcg acaagatcat caccagcacc agcgacttcc agacctggtg gaagaacttc     540
gccactcagt tcaagagcaa cagcaaggtg atcttcgaca ccaacaacga gtacaacacc     600
atggaccaga ccctggtgct gaacctgaac caggccgcca tcaacggcat cagggcagct     660
ggcgccaccc agaccatctt cgtggagggc aaccagtgga gcggcgcctg gtcctggcca     720
gacgtgaacg acaacatgaa ggccctgacc gacccgctgg acaagatcgt gtacgagatg     780
caccagtacc tggacagcga cagcagcggc accagcccga actgcgtgtc caccaccatc     840
ggcgtggaga gggtgaaggc cgccaccgag tggctgcgca agaacaagaa gatcggcatg     900
atcggcgagc tggctggcgg cccaaacgac acctgcaaga ccgccgtgaa gaacatgctg     960
gactacctga aggaaaacag cgatgtctgg aagggcgtga cctggtgggc cgctggccca    1020
tggtgggccg actacatgtt cagcttcgag ccgccaagcg gcaccggcta ccagtactac    1080
aacagcctgc tcaagaccta catc                                          1104
```

<210> SEQ ID NO 30
<211> LENGTH: 1287
<212> TYPE: DNA
<213> ORGANISM: Artificial Sequence
<220> FEATURE:
<223> OTHER INFORMATION: Synthetic construct, BD25CC2, nucleic acid

<400> SEQUENCE: 30

```
atggcccaga acgccgcctg ggctcaatgc ggcggcaacg gctggaccgg cagcaagacc      60
tgcgtgtccg gctacaagtg caccgtggtg aacgagtggt actcccagtg catcccgggc     120
accgccgagg aacctaccac caccctcaag accaccaccg gcggcggcag cacccccaacc   180
ggccgggcca agcagctgga ggacaaggtc gaggagctgc tgagcaagaa ctaccacctg     240
gagaacgagg tcgcgaggct gaagaaactg gtcggaccag caacggcaa gttcctgtgg     300
gtgggcacga acgaggctgg cggcgagttc ggcgagggca gcctgccagg cacctggggc     360
aagcacttca tcttcccgga cccagccgcc gtggacaccc tgatcagcca gggctacaac     420
gccttccgcg tccagctgcg catggagcgc accaacccga gcagcatgac cggccccttc     480
gacaccgcct acctgaagaa cctgaccacc atcgtggacc acatcaccgg caagggcgcc     540
aacgtgatcc tggacccgca caactacggc cgctacttcg acaagatcat caccagcacc     600
agcgacttcc agacctggtg gaagaacttc gccactcagt tcaagagcaa cagcaaggtg     660
atcttcgaca ccaacaacga gtacaacacc atggaccaga ccctggtgct gaacctgaac     720
caggccgcca tcaacggcat cagggcagct ggcgccaccc agaccatctt cgtggagggc     780
aaccagtgga gcggcgcctg gtcctggcca gacgtgaacg acaacatgaa ggccctgacc     840
gacccgctgg acaagatcgt gtacgagatg caccagtacc tggacagcga cagcagcggc     900
```

-continued

```
accagcccga actgcgtgtc caccaccatc ggcgtggaga gggtgaaggc cgccaccgag      960
tggctgcgca agaacaagaa gatcggcatg atcggcgagc tggctggcgg cccaaacgac     1020
acctgcaaga ccgccgtgaa gaacatgctg gactacctga aggaaaacag cgatgtctgg     1080
aagggcgtga cctggtgggc cgctggccca tggtgggccg actacatgtt cagcttcgag     1140
ccgccaagcg gcaccggcta ccagtactac aacagcctgc tcaagaccta catcgggtct     1200
caattggaag ataaagtgga agagctcctg tccaaaaatt atcatctgga aaatgaggtg     1260
gcccgcttga agaaattggt cgggtga                                         1287
```